(12) United States Patent
Morieux et al.

(10) Patent No.: US 10,453,560 B2
(45) Date of Patent: Oct. 22, 2019

(54) CONTEXT-AWARE VIRTUAL KEYBOARD FOR CHEMICAL STRUCTURE DRAWING APPLICATIONS

(71) Applicant: PerkinElmer Informatics, Inc., Waltham, MA (US)

(72) Inventors: Pierre Morieux, Strasbourg (FR); Michael Wilson, Norton, MA (US); Jeffrey F. Lowrie, South Easton, MA (US)

(73) Assignee: PerkinElmer Informatics, Inc., Waltham, MA (US)

( * ) Notice: Subject to any disclaimer, the term of this patent is extended or adjusted under 35 U.S.C. 154(b) by 97 days.

(21) Appl. No.: 15/884,191

(22) Filed: Jan. 30, 2018

(65) Prior Publication Data

US 2019/0236244 A1  Aug. 1, 2019

(51) Int. Cl.
*G06F 3/0484* (2013.01)
*G16C 20/80* (2019.01)
*G06F 3/0488* (2013.01)
*G16C 20/70* (2019.01)

(52) U.S. Cl.
CPC ........... *G16C 20/80* (2019.02); *G06F 3/0484* (2013.01); *G06F 3/04886* (2013.01); *G16C 20/70* (2019.02)

(58) Field of Classification Search
CPC ...... G06F 19/26; G06F 19/708; G06F 19/701; G06F 19/702
See application file for complete search history.

(56) References Cited

U.S. PATENT DOCUMENTS

| | | | | |
|---|---|---|---|---|
| 4,085,443 A * | 4/1978 | Dubois | ................. | G06F 3/0219 345/168 |
| 5,461,580 A * | 10/1995 | Facci | ..................... | G06T 17/00 703/2 |
| 2007/0192747 A1* | 8/2007 | Phelan | ................... | G06F 15/16 715/847 |
| 2009/0177455 A1* | 7/2009 | Banerjee | ................ | G06T 13/20 703/12 |
| 2013/0222265 A1* | 8/2013 | Smith | .................... | G16C 20/80 345/173 |
| 2014/0337725 A1* | 11/2014 | Smith | ................... | G06F 3/0484 715/702 |

* cited by examiner

*Primary Examiner* — Scott T Baderman
*Assistant Examiner* — Pritisha N Parbadia
(74) *Attorney, Agent, or Firm* — Banner & Witcoff, Ltd.

(57) ABSTRACT

Described herein are systems, methods, and apparatus for electronically drawing and editing representations of chemical structures using an intuitive user interface. This user interface, the context-aware virtual keyboard, makes it faster and easier to draw and edit chemical structure representations by guiding the user through the sequence of steps required to produce the representation in a context-based, non-linear fashion. The context-based virtual keyboard allows a user to quickly create graphical representations of complex chemical structures by using the structure itself as a basis for presenting efficient options for subsequent drawing/editing steps. Different possible and/or likely actions (e.g., edits to a chemical structure being drawn) are presented to the user based on a selected navigation position on the drawing. Thus, a user can efficiently and intuitively modify a chemical structure drawing without the tedious manual selection of portions of the chemical structure and without searching through complicated menus.

35 Claims, 24 Drawing Sheets

Predefined chemical structure representations

Drawing a new molecule from scratch

FIG. 4

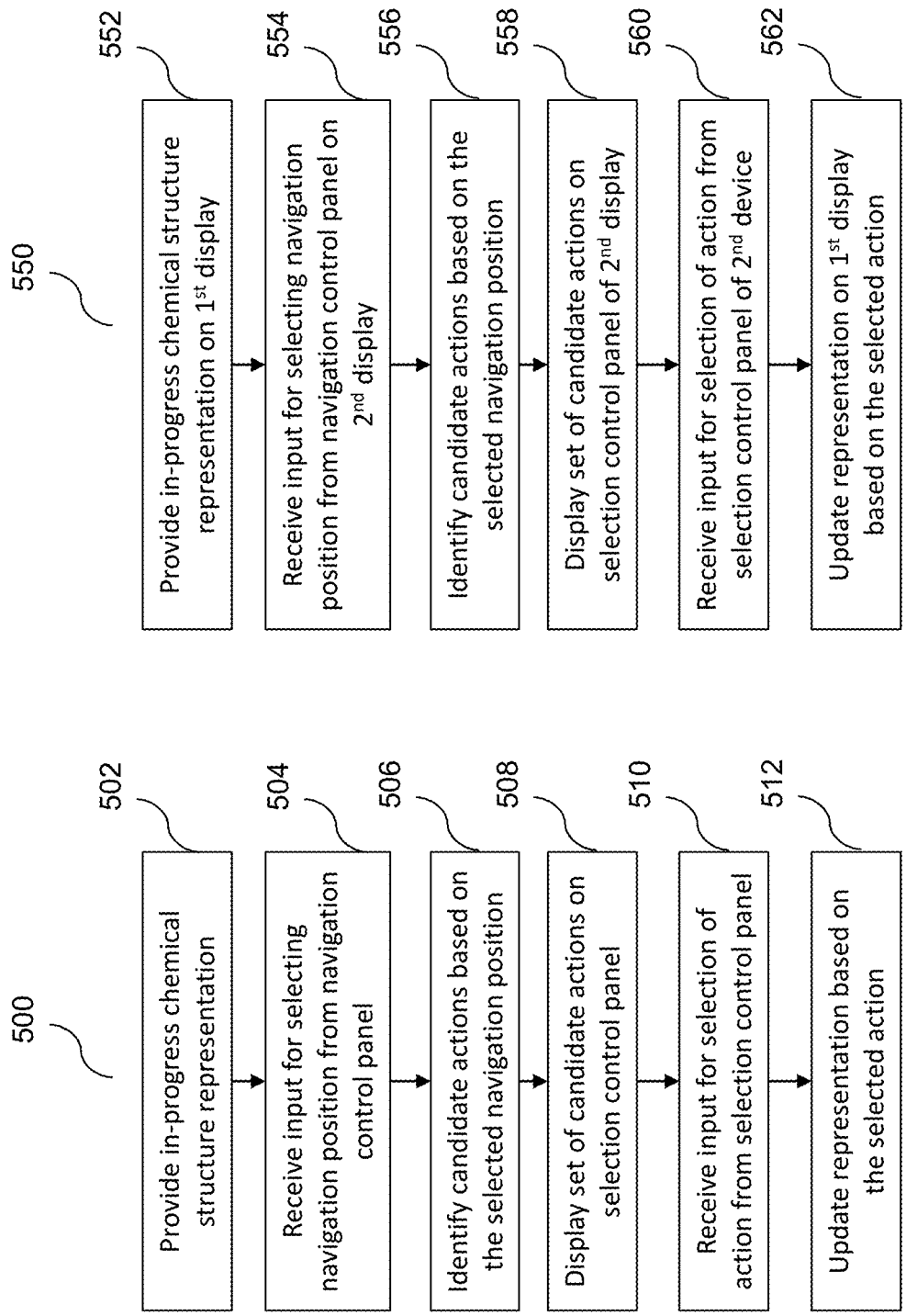

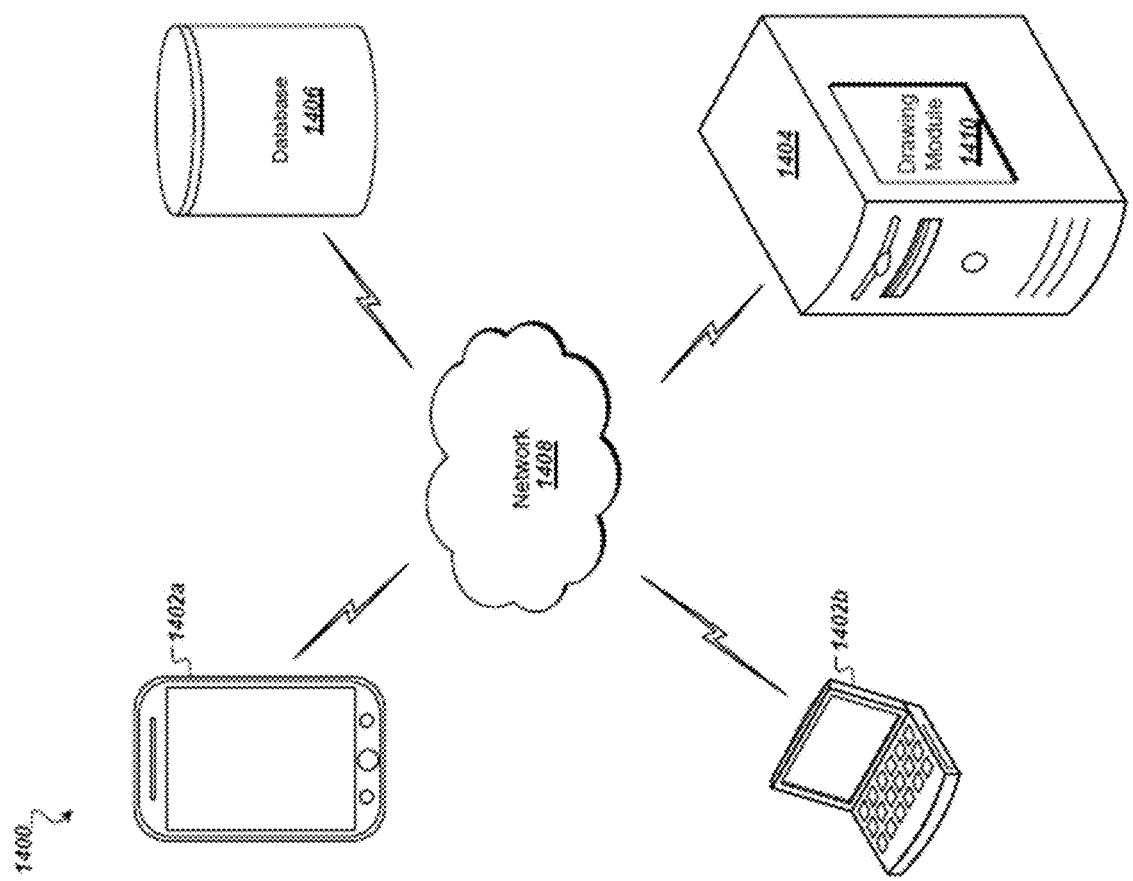

CONTEXT-AWARE VIRTUAL KEYBOARD FOR CHEMICAL STRUCTURE DRAWING APPLICATIONS

FIELD OF THE INVENTION

This invention relates generally to systems, methods, and apparatus for drawing and/or editing representations of chemical structures. More specifically, described herein are systems, methods, and apparatus for creating and editing representations of chemical structures using a context-aware virtual keyboard.

BACKGROUND

Chemical structure rendering software is widely used by research and educational institutions to depict chemical structures and chemical reactions of interest. Unlike chemical formulas or chemical names, structural formulas provide a graphical representation of a molecular structure. A graphical chemical structure representation is capable of indicating the arrangements of atoms in a way that a chemical formula cannot.

Current methods for drawing and editing representations of chemical structures on a computer require a user to perform many repetitive tasks in order to manually create structures using a set of software "tools" that serve similar functions as the physical drawing tools used to create a drawing on paper. For example, these methods utilize mouse-driven or touchpad-based commands that include pointing and clicking on displayed menu items and/or on portions of the chemical structure representation in a graphical user interface. Existing chemical structure rendering applications for handheld electronic devices, e.g., tablet computers and smartphones, use this same manual paradigm. These applications can be clumsy when attempting to draw complex chemical structures that include many bonds and elements, particularly on small touchscreen devices. There is a need for more efficient and intuitive methods for drawing and editing representations of chemical structures.

SUMMARY

Described herein are systems, methods, and apparatus for electronically drawing and editing representations of chemical structures using an intuitive user interface. This user interface, the context-aware virtual keyboard, makes it faster and easier to draw and edit chemical structure representations by guiding the user through the sequence of steps required to produce the representation in a context-based, non-linear fashion. The context-based virtual keyboard allows a user to quickly create graphical representations of complex chemical structures by using the structure itself as a basis for presenting efficient options for subsequent drawing/editing steps. Different possible and/or likely actions (e.g., edits to a chemical structure being drawn) are presented to the user based on a selected navigation position on the drawing. Thus, a user can efficiently and intuitively modify a chemical structure drawing without the tedious manual selection of portions of the chemical structure and without searching through complicated menus.

Rather than relying on the ability of a user to manually select discrete portions (e.g., atoms or bonds) of a complex chemical structure, navigation is performed using a specially designed navigation control panel. This navigation panel allows users to quickly and easily select portions of chemical structure representations on small touchscreen devices such as smart phones and tablet computers. Manually selecting discrete portions of a chemical structure representation on a touchscreen device is often painstaking using existing technologies, which typically require a user to manually select (e.g. with the tip of a finger) a specific portion of a complex chemical structure that is presented on a small display. For example, it can very difficult to accurately select a specific bond or atom in a large chemical structure that is presented to a user on a small display (e.g., a smartphone display with a display area of about 100 $cm^2$ or less); the navigation control panel described herein solves this problem.

By offering a user a limited set of likely and/or possible options in a user-friendly, intuitive manner, the systems, methods, and apparatus described herein provide efficient and accurate tools for drawing and editing chemical structures. Based on the navigation position (e.g., selected using the navigation control panel described herein), a manageable subset of possible and/or likely actions are identified and presented to the user as options for editing an in-progress chemical structure drawing. Since the subset of actions is identified based on the context of the drawing (e.g., based on the navigation position selected by the user), the number of actions in the subset is relatively small (e.g., 20 or fewer). Each of these actions is displayed as an easily interpretable icon using known visual nomenclature (e.g., using known chemical symbols, abbreviations, and/or chemical structure drawings). The set of displayed icons fits in a small display region and at an appropriate size (e.g., about 30 to about 50 pixels) for viewing and selecting, for example, on the touchscreen of a smartphone or tablet computer. The chemical structure drawing can then be intuitively edited by choosing a desired action (e.g., adding a carbon ring, a chemical bond, or an atom) without requiring the user to search through menus of possible actions or memorize hotkeys for every possible action. The control components and interface of the context-aware virtual keyboard described herein thus simplify and standardize the repetitive task of creating chemical structure representations.

In various embodiments, the systems, methods, and apparatus described herein utilize or include a tablet computer, a mobile phone (e.g., smartphone) device, or any other computer device or system capable of receiving input. In certain embodiments, the systems, methods, and apparatus utilize a handheld touch-sensitive device (e.g., a tablet computer or a mobile phone device) for receiving user input and a separate device for displaying the representation of a chemical structure. The systems, methods, and apparatus have applications in a wide variety of industries that create and edit structural formulas, such as the reagent industry, the publishing industry, and/or the web search industry.

Elements of embodiments described with respect to a given aspect of the invention may be used in various embodiments of another aspect of the invention. For example, it is contemplated that features of dependent claims depending from one independent claim can be used in apparatus, articles, systems, and/or methods of any of the other independent claims.

In one aspect, the present disclosure is directed to an apparatus for creating and/or editing a graphical representation of a chemical structure using a context-aware virtual keyboard, the apparatus comprising: a memory for storing a set of instructions; and a processor for executing the set of instructions. The instructions, when executed, cause the processor to: provide a graphical representation of at least a portion of an in-progress chemical structure for presentation on a graphical display in a canvas panel of the context-aware virtual keyboard; receive an input, from a navigation control panel of the context-aware virtual keyboard, corresponding to a selection of a navigation position, wherein the navigation position corresponds to the location of an atom, a chemical bond, a chemical structure portion, or a reaction arrow in the graphical representation; identify, based at least in part on the selected navigation position, a set of candidate actions and display the set of candidate actions on the graphical display (e.g., as action icons) in a selection control panel of the context-aware virtual keyboard; receive an input from the selection control panel of the context-aware virtual keyboard corresponding to a selection of an action from the set of candidate actions; and update the graphical representation based on the selected action by: (i) appending a chemical structure associated with the selected action to the in-progress chemical structure at an atom, chemical bond, or chemical structure portion corresponding to the navigation position, and/or (ii) replacing or partially replacing the atom, chemical bond, or chemical structure portion corresponding to the navigation position in the in-progress chemical structure with the chemical structure associated with the selected action, and/or (iii) modifying the atom, chemical bond, chemical structure portion, or a reaction arrow corresponding to the navigation position in the in-progress chemical structure according to the selected action.

In certain embodiments, each action of the set of candidate actions corresponds to a modification to the location of the atom, chemical bond, chemical structure portion, or reaction arrow corresponding to the selected navigation position.

In certain embodiments, the set of candidate actions comprise one or more members selected from the group consisting of (i) adding a carbon ring, (ii) adding a chemical bond, (iii) adding an atom, (iv) adding a text entry, (v) changing a bond angle, (vi) changing a chemical bond type (e.g., between a single, double, or triple bond), (vii) rotating a chemical bond by an angle, and (viii) flipping a chemical bond around an axis.

In certain embodiments, the instructions, when executed, cause the processor to update the set of candidate actions in real-time based on the selected navigation position.

In certain embodiments, when the navigation position corresponds to the location of an atom, the set of candidate actions comprise one or more members selected from the group consisting of (i) adding a carbon ring, (ii) adding a chemical bond, (iii) adding an atom, and (iv) adding a text entry.

In certain embodiments, when the navigation position corresponds to the location of a first chemical bond, the set of candidate actions comprise one or more members selected from the group consisting of (i) adding a carbon ring, (ii) adding a second chemical bond, (iii) adding an atom, (iv) adding a text entry, (v) changing an angle of the first chemical bond, (vi) changing a bond type of the first chemical bond (e.g., between a single, double, or triple bond, e.g., between a bold bond, a wavy bond, a dashed bond, a hashed wedged bond, and a wedged bond), (vii) rotating the first chemical bond by an angle, and (viii) flipping the first chemical bond around an axis.

In certain embodiments, when the navigation position corresponds to the location of a chemical structure portion, the set of candidate actions comprise one or more members selected from the group consisting of (i) selecting a different chemical structure portion, (ii) creating a reaction, (iii) duplicating the chemical structure portion, and (iv) joining the chemical structure portion to a different chemical structure portion at a bond or atom.

In certain embodiments, when the navigation position corresponds to the location of a reaction arrow, the set of candidate actions comprise one or more members selected from the group consisting of (i) adding reaction conditions and (ii) adding associated reagents and/or reactants.

In certain embodiments, each action of the set of candidate actions is derived from an evaluation of whether the action is chemically feasible.

In certain embodiments, each action of the set of candidate actions is derived from an evaluation of whether it is chemically feasible to (i) append, to an atom, bond, or chemical structure portion associated with the selected navigation position, a chemical structure associated with the action or (ii) replace or partially replace the atom, bond, or chemical structure portion associated with the selected navigation position with the atom, bond, or chemical structure portion structure associated with the action.

In certain embodiments, the instructions, when executed, cause the processor to arrange the set of candidate actions in a ranked order for rendering on the graphical display.

In certain embodiments, the instructions, when executed, cause the processor to arrange the set of candidate actions in a ranked order and display a selection of the top ranked candidate actions on the graphical display as predictive action icons (e.g., predictive action buttons).

In certain embodiments, each action of the set of candidate actions is derived from a document using a parsing technique.

In certain embodiments, the instructions, when executed, cause the processor to identify a plurality of predictive actions, wherein each predictive action of the plurality of predictive actions is derived from a database and/or based on a frequency of use by one or more users; and display one or more predictive actions from the plurality in or above the selection control panel of the context-aware virtual keyboard on the graphical display.

In certain embodiments, three or fewer predictive actions are displayed in or above the selection control panel of the context-aware virtual keyboard on the graphical display.

In certain embodiments, the instructions, when executed, cause the processor to display a chemical structure associated with one of the plurality of predictive actions as being appended to the in-progress chemical structure.

In certain embodiments, the canvas panel, navigation control panel, and selection control panel are displayed in separate windows on the graphical display.

In certain embodiments, the canvas panel is larger than the navigation control panel and the selection control panel.

In certain embodiments, the canvas panel comprises 50% or more of the display area of the graphical display.

In certain embodiments, the navigation control panel and selection control panel are overlaid (e.g., superimposed) over the canvas panel (e.g., to allow for the canvas panel, navigation control panel, and selection control panel to fit on a cell phone display).

In certain embodiments, the navigation control panel comprises a plurality of navigation icons (e.g., navigation buttons).

In certain embodiments, each of the plurality of navigation icons has a display area in a range from about 30 to about 50 pixels.

In certain embodiments, the navigation control panel comprises directional arrows or a "navigation wheel" for selecting the navigation position.

In certain embodiments, the navigation control panel comprises ancillary action buttons for one or more the actions selected from the group consisting of (i) deleting an atom, bond, or portion of the chemical structure corresponding to the navigation position, (ii) adding a reaction, (iii) undoing a previous action, (iv) redoing a previous action, and (v) selecting an atom, bond, or portion of the chemical structure.

In certain embodiments, the navigation control panel comprises 12 icons or less.

In certain embodiments, the set of candidate actions are displayed as a plurality of action icons (e.g., action buttons) in the selection control panel.

In certain embodiments, each of the plurality of action icons (e.g., action buttons) has a display area in a range from about 30 to about 50 pixels.

In certain embodiments, the selection control panel comprises 20 action icons (e.g., action buttons) or less.

In certain embodiments, the selection control panel displays 20 icons or less on each of a plurality of selection screens, and comprises a scroll icon for switching between the selection screens.

In certain embodiments, the graphical display has a display region of about 700 $cm^2$ or less in area [e.g., wherein the graphical display is a display of a tablet computer with a display region of about 700 $cm^2$ or less in area (e.g., a 12.9-inch Apple® iPad Pro® by Apple Inc. of Cupertino, Calif. has a display with dimensions of about 300 mm×220 mm or a display region of about 660 $cm^2$ in area)].

In certain embodiments, the graphical display has a display region of about 150 $cm^2$ or less in area [e.g., wherein the graphical display is a display of a tablet computer with a display region of about 150 $cm^2$ or less in area (e.g., an Apple® iPhone X® by Apple Inc. of Cupertino, Calif. has a display with dimensions of about 140 mm×70 mm or a display region of about 100 $cm^2$ in area)].

In certain embodiments, the graphical display is a touchscreen.

In certain embodiments, the instructions, when executed, cause the processor to receive the input over a network, from a computing device.

In certain embodiments, the computing device comprises a touchscreen.

In certain embodiments, the computing device is a cell phone or a tablet computer.

In certain embodiments, the set of candidate actions are stored in the memory.

In certain embodiments, the instructions, when executed, cause the processor to receive an input from the selection control panel of the context-aware virtual keyboard corresponding to a selection of a portion of the in-progress chemical structure; receive an input from the selection control panel of the context-aware virtual keyboard corresponding to a selection of a reaction icon; and update the representation, based on the one or more selected portions and the selected reaction icon, by (i) appending an arrow to the right of the in-progress chemical structure and (ii) appending a copy of the selected portion to the right of the arrow.

In certain embodiments, the instructions, when executed, cause the processor to receive an input from the selection control panel of the context-aware virtual keyboard corresponding to a selection of two or more portions of the in-progress chemical structure; receive an input from the selection control panel of the context-aware virtual keyboard corresponding to a selection of a reaction icon; and update the representation, based on the one or more selected portions and the selected reaction icon, by (i) appending an arrow to the right of the in-progress chemical structure and (ii) appending a reaction product to the right of the arrow, wherein the reaction product corresponds to a chemical structure resulting from the reaction of the two or more selected portions and is derived from predefined chemical rules.

In one aspect, the present disclosure is directed to an apparatus for creating and/or editing a graphical representation of a chemical structure using a dual-display context-aware virtual keyboard, the apparatus comprising: a memory for storing a set of instructions; and a processor for executing the set of instructions. The instructions, when executed, cause the processor to: provide a graphical representation of at least a portion of an in-progress chemical structure for presentation on a first graphical display[e.g., wherein the first computing device has a display region at least 1400 $cm^2$ in area (e.g., a 22 inch computer monitor has dimensions of about 47 cm×30 cm or a display region of about 1410 $cm^2$ in area)], receive an input, from a computing device [e.g., a touchscreen device, e.g., a handheld touchscreen device (e.g., a device with a graphical display with a display region of about 150 $cm^2$ or less in area)] displaying, on a second graphical display, a navigation control panel of the context-aware virtual keyboard, said input corresponding to a selection of a navigation position, wherein the navigation position corresponds to the location of an atom, bond, chemical structure portion, or reaction arrow in the graphical representation; identify, based on the selected navigation position, a set of candidate actions and display the set of candidate actions on the second graphical display in a selection control panel of the context-aware virtual keyboard; receive an input, via the selection control panel of the context-aware virtual keyboard displayed on the second graphical display, corresponding to a selection of an action from the set of candidate actions; and update the graphical representation, displayed on the first graphical display, based on the selected action by: (i) appending a chemical structure associated with the selected action to the in-progress chemical structure at an atom, bond, or chemical structure portion corresponding to the navigation position, and/or (ii) replacing or partially replacing the atom, bond, or chemical structure portion corresponding to the navigation position in the in-progress chemical structure with the chemical structure associated with the selected action, and/or (iii) modifying the atom, bond, chemical structure portion, or a reaction arrow corresponding to the navigation position in the in-progress chemical structure according to the selected action.

In certain embodiments, the first graphical display has a display region of about 1400 $cm^2$ or greater in area (e.g., a 22 inch computer monitor has dimensions of about 47 cm×30 cm or a display region of about 1410 $cm^2$ in area)].

In certain embodiments, the second graphical display has a display region of about 150 $cm^2$ [e.g., wherein the second graphical display is a display of a tablet computer with a display region of about 150 $cm^2$ or less in area (e.g., an Apple® iPhone X® by Apple Inc. of Cupertino, Calif. has a display with dimensions of about 140 mm×70 mm or a display region of about 100 $cm^2$ in area)] or less in area.

In certain embodiments, the first graphical display is a computer monitor, a television, or a projected image.

In certain embodiments, the second graphical display is a touchscreen display of a mobile phone or a tablet computer.

In certain embodiments, each action of the set of candidate actions corresponds to a modification to the location of the atom, chemical bond, chemical structure portion, or reaction arrow corresponding to the selected navigation position.

In certain embodiments, the set of candidate actions comprise one or more members selected from the group consisting of (i) adding a carbon ring, (ii) adding a chemical bond, (iii) adding an atom, (iv) adding a text entry, (v) changing a bond angle, (vi) changing a chemical bond type (e.g., between a single, double, or triple bond), (vii) rotating a chemical bond by an angle, and (viii) flipping a chemical bond around an axis.

In certain embodiments, the instructions, when executed, cause the processor to update the set of candidate actions in real-time based on the selected navigation position.

In certain embodiments, when the navigation position corresponds to the location of an atom, the set of candidate actions comprise one or more members selected from the group consisting of (i) adding a carbon ring, (ii) adding a chemical bond, (iii) adding an atom, and (iv) adding a text entry.

In certain embodiments, when the navigation position corresponds to the location of a first chemical bond, the set of candidate actions comprise one or more members selected from the group consisting of (i) adding a carbon ring, (ii) adding a second chemical bond, (iii) adding an atom, (iv) adding a text entry, (v) changing an angle of the first chemical bond, (vi) changing a bond type of the first chemical bond (e.g., between a single, double, or triple bond, e.g., between a bold bond, a wavy bond, a dashed bond, a hashed wedged bond, and a wedged bond), (vii) rotating the first chemical bond by an angle, and (viii) flipping the first chemical bond around an axis.

In certain embodiments, when the navigation position corresponds to the location of a chemical structure portion, the set of candidate actions comprise one or more members selected from the group consisting of (i) selecting a different chemical structure portion, (ii) creating a reaction, (iii) duplicating the chemical structure portion, and (iv) joining the chemical structure portion to a different chemical structure portion at a bond or atom.

In certain embodiments, when the navigation position corresponds to the location of a reaction arrow, the set of candidate actions comprise one or more members selected from the group consisting of (i) adding reaction conditions and (ii) adding associated reagents and/or reactants.

In certain embodiments, each action of the set of candidate actions is derived from an evaluation of whether the action is chemically feasible.

In certain embodiments, each action of the set of candidate actions is derived from an evaluation of whether it is chemically feasible to (i) append, to an atom, bond, or chemical structure portion associated with the selected navigation position, a chemical structure associated with the action or (ii) replace or partially replace the atom, bond, or chemical structure portion associated with the selected navigation position with the atom, bond, or chemical structure portion structure associated with the action.

In certain embodiments, the instructions, when executed, cause the processor to arrange the set of candidate actions in a ranked order for rendering on the second graphical display.

In certain embodiments, the instructions, when executed, cause the processor to arrange the set of candidate actions in a ranked order and display a selection of the top ranked candidate actions on the second graphical display as predictive action icons (e.g., predictive action buttons).

In certain embodiments, each action of the set of candidate actions is derived from a document using a parsing technique.

In certain embodiments, the instructions, when executed, cause the processor to identify a plurality of predictive actions, wherein each predictive action of the plurality of predictive actions is derived from a database and/or based on a frequency of use by one or more users; and display one or more predictive actions from the plurality in or above the selection control panel of the context-aware virtual keyboard on the second graphical display.

In certain embodiments, the instructions, when executed, cause the processor to display a chemical structure associated with one of the plurality of predictive actions as being appended to the in-progress chemical structure.

In certain embodiments, the navigation control panel comprises a plurality of navigation icons (e.g., navigation buttons).

In certain embodiments, each of the plurality of navigation icons has a display area in a range from about 30 to about 50 pixels.

In certain embodiments, the navigation control panel comprises directional arrows or a "navigation wheel" for selecting the navigation position.

In certain embodiments, the navigation control panel comprises ancillary action buttons for one or more the actions selected from the group consisting of (i) deleting an atom, bond, or portion of the chemical structure corresponding to the navigation position, (ii) adding a reaction, (iii) undoing a previous action, (iv) redoing a previous action, and (v) selecting an atom, bond, or portion of the chemical structure.

In certain embodiments, the navigation control panel comprises 12 icons or less.

In certain embodiments, the set of candidate actions are displayed as a plurality of action icons (e.g., action buttons) in the selection control panel.

In certain embodiments, each of the plurality of action icons (e.g., action buttons) has a display area in a range from about 30 to about 50 pixels.

In certain embodiments, the selection control panel comprises 20 action icons (e.g., action buttons) or less.

In certain embodiments, the selection control panel displays 20 icons or less on each of a plurality of selection screens, and comprises a scroll icon for switching between the selection screens.

In certain embodiments, the set of candidate actions are stored in the memory.

In certain embodiments, the first graphical display is larger than the second graphical display.

In one aspect, the present disclosure is directed to a method of creating a graphical representation of a chemical structure using a context-aware virtual keyboard. The method comprises: providing, by a processor of a computing device, a graphical representation of at least a portion of an in-progress chemical structure for presentation on a graphical display in a canvas panel of the context-aware virtual keyboard; receiving, by the processor, an input, from a navigation control panel of the context-aware virtual keyboard, corresponding to a selection of a navigation position, wherein the navigation position corresponds to the location of an atom, a bond, a chemical structure portion, or a reaction arrow in the graphical representation; identifying, by the processor, based at least in part on the selected navigation position, a set of candidate actions and display the set of candidate actions on the graphical display (e.g., as action icons) in a selection control panel of the context-aware virtual keyboard; receiving, by the processor, an input from the selection control panel of the context-aware virtual keyboard corresponding to a selection of an action from the set of candidate actions; and updating, by the processor, the graphical representation based on the selected action by: (i) appending a chemical structure associated with the selected action to the in-progress chemical structure at an atom, bond, or chemical structure portion corresponding to the navigation position, and/or (ii) replacing or partially replacing the atom, bond, or chemical structure portion corresponding to the navigation position in the in-progress chemical structure with the chemical structure associated with the selected action, and/or (iii) modifying the atom, bond, chemical structure portion, or a reaction arrow corresponding to the navigation position in the in-progress chemical structure according to the selected action.

In certain embodiments, receiving the graphical representation of the in-progress chemical structure comprises importing the chemical structure from an electronic laboratory notebook (ELN) system.

In certain embodiments, receiving the graphical representation of the in-progress chemical structure comprises receiving the graphical representation of the chemical structure from a registration system having identified and stored the graphical representation of the chemical structure.

In certain embodiments, each action of the set of candidate actions corresponds to a modification to the location of the atom, chemical bond, chemical structure portion, or reaction arrow corresponding to the selected navigation position.

In certain embodiments, the set of candidate actions comprise one or more members selected from the group consisting of (i) adding a carbon ring, (ii) adding a chemical bond, (iii) adding an atom, (iv) adding a text entry, (v) changing a bond angle, (vi) changing a chemical bond type (e.g., between a single, double, or triple bond), (vii) rotating a chemical bond by an angle, and (viii) flipping a chemical bond around an axis.

In certain embodiments, the method comprises updating the set of candidate actions in real-time based on the selected navigation position.

In certain embodiments, when the navigation position corresponds to the location of an atom, the set of candidate actions comprise one or more members selected from the group consisting of (i) adding a carbon ring, (ii) adding a chemical bond, (iii) adding an atom, and (iv) adding a text entry.

In certain embodiments, when the navigation position corresponds to the location of a first chemical bond, the set of candidate actions comprise one or more members selected from the group consisting of (i) adding a carbon ring, (ii) adding a second chemical bond, (iii) adding an atom, (iv) adding a text entry, (v) changing an angle of the first chemical bond, (vi) changing a bond type of the first chemical bond (e.g., between a single, double, or triple bond, e.g., between a bold bond, a wavy bond, a dashed bond, a hashed wedged bond, and a wedged bond), (vii) rotating the first chemical bond by an angle, and (viii) flipping the first chemical bond around an axis.

In certain embodiments, when the navigation position corresponds to the location of a chemical structure portion, the set of candidate actions comprise one or more members selected from the group consisting of (i) selecting a different chemical structure portion, (ii) creating a reaction, (iii) duplicating the chemical structure portion, and (iv) joining the chemical structure portion to a different chemical structure portion at a bond or atom.

In certain embodiments, when the navigation position corresponds to the location of a reaction arrow, the set of candidate actions comprise one or more members selected from the group consisting of (i) adding reaction conditions and (ii) adding associated reagents and/or reactants.

In certain embodiments, each action of the set of candidate actions is derived from an evaluation of whether the action is chemically feasible.

In certain embodiments, each action of the set of candidate actions is derived from an evaluation of whether it is chemically feasible to (i) append, to an atom, bond, or chemical structure portion associated with the selected navigation position, a chemical structure associated with the action or (ii) replace or partially replace the atom, bond, or chemical structure portion associated with the selected navigation position with the atom, bond, or chemical structure portion structure associated with the action.

In certain embodiments, the method comprises arranging the set of candidate actions in a ranked order for rendering on the graphical display.

In certain embodiments, the method comprises arranging the set of candidate actions in a ranked order and display a selection of the top ranked candidate actions on the graphical display as predictive action icons (e.g., predictive action buttons).

In certain embodiments, each action of the set of candidate actions is derived from a document using a parsing technique.

In certain embodiments, the method comprises identifying a plurality of predictive actions, wherein each predictive action of the plurality of predictive actions is derived from a database and/or based on a frequency of use by one or more users; and displaying one or more predictive actions from the plurality in or above the selection control panel of the context-aware virtual keyboard on the graphical display.

In certain embodiments, three or fewer predictive actions are displayed in or above the selection control panel of the context-aware virtual keyboard on the graphical display.

In certain embodiments, the method comprises displaying a chemical structure associated with one of the plurality of predictive actions as being appended to the in-progress chemical structure.

In certain embodiments, the canvas panel, navigation control panel, and selection control panel are displayed in separate windows on the graphical display.

In certain embodiments, the canvas panel is larger than the navigation control panel and the selection control panel.

In certain embodiments, the canvas panel comprises 50% or more of the display area of the graphical display.

In certain embodiments, the navigation control panel and selection control panel are overlaid (e.g., superimposed) over the canvas panel (e.g., to allow for the canvas panel, navigation control panel, and selection control panel to fit on a cell phone display).

In certain embodiments, the navigation control panel comprises a plurality of navigation icons (e.g., navigation buttons).

In certain embodiments, each of the plurality of navigation icons has a display area in a range from about 30 to about 50 pixels.

In certain embodiments, the navigation control panel comprises directional arrows or a "navigation wheel" for selecting the navigation position.

In certain embodiments, the navigation control panel comprises ancillary action buttons for one or more the actions selected from the group consisting of (i) deleting an atom, bond, or portion of the chemical structure corresponding to the navigation position, (ii) adding a reaction, (iii) undoing a previous action, (iv) redoing a previous action, and (v) selecting an atom, bond, or portion of the chemical structure.

In certain embodiments, the navigation control panel comprises 12 icons or less.

In certain embodiments, the set of candidate actions are displayed as a plurality of action icons (e.g., action buttons) in the selection control panel.

In certain embodiments, each of the plurality of action icons (e.g., action buttons) has a display area in a range from about 30 to about 50 pixels.

In certain embodiments, the selection control panel comprises 20 action icons (e.g., action buttons) or less.

In certain embodiments, the selection control panel displays 20 icons or less on each of a plurality of selection screens, and comprises a scroll icon for switching between the selection screens.

In certain embodiments, the graphical display has a display region of about 700 $cm^2$ or less in area [e.g., wherein the graphical display is a display of a tablet computer with a display region of about 700 $cm^2$ or less in area (e.g., a 12.9-inch Apple® iPad Pro® by Apple Inc. of Cupertino, Calif. has a display with dimensions of about 300 mm×220 mm or a display region of about 660 $cm^2$ in area)].

In certain embodiments, the graphical display has a display region of about 150 $cm^2$ or less in area [e.g., wherein the graphical display is a display of a tablet computer with a display region of about 150 $cm^2$ or less in area (e.g., an Apple® iPhone X® by Apple Inc. of Cupertino, Calif. has a display with dimensions of about 140 mm×70 mm or a display region of about 100 $cm^2$ in area)].

In certain embodiments, the graphical display is a touchscreen.

In certain embodiments, the computing device comprises a touchscreen.

In one aspect, the present disclosure is directed to a method of creating a graphical representation of a chemical structure using a dual-display context-aware virtual keyboard. The method comprises: providing, by a processor of a computing device, a graphical representation of at least a portion of an in-progress chemical structure for presentation on a first graphical display [e.g., wherein the first computing device has a display region at least 1400 $cm^2$ in area (e.g., a 22 inch computer monitor has dimensions of about 47 cm×30 cm or a display region of about 1410 $cm^2$ in area)]; receiving, by the processor, an input, from a computing device [e.g., a touchscreen device, e.g., a handheld touchscreen device (e.g., a device with a graphical display with a display region of about 150 $cm^2$ or less in area)] displaying, on a second graphical display, a navigation control panel of the context-aware virtual keyboard, said input corresponding to a selection of a navigation position, wherein the navigation position corresponds to the location of an atom, bond, chemical structure portion, or reaction arrow in the graphical representation; identifying, by the processor, based on the selected navigation position, a set of candidate actions and displaying the set of candidate actions on the second graphical display in a selection control panel of the context-aware virtual keyboard; receiving, by the processor, an input, via the selection control panel of the context-aware virtual keyboard displayed on the second graphical display, corresponding to a selection of an action from the set of candidate actions; and updating, by the processor, the representation, displayed on the first graphical display, based on the selected action by: (i) appending a chemical structure associated with the selected action to the in-progress chemical structure at an atom, bond, or chemical structure portion corresponding to the navigation position, and/or (ii) replacing or partially replacing the atom, bond, or chemical structure portion corresponding to the navigation position in the in-progress chemical structure with the chemical structure associated with the selected action, and/or (iii) modifying the atom, bond, chemical structure portion, or a reaction arrow corresponding to the navigation position in the in-progress chemical structure according to the selected action.

In certain embodiments, receiving the graphical representation of the in-progress chemical structure comprises importing the chemical structure from an electronic laboratory notebook (ELN) system.

In certain embodiments, receiving the graphical representation of the in-progress chemical structure comprises receiving the graphical representation of the chemical structure from a registration system having identified and stored the graphical representation of the chemical structure.

In certain embodiments, each action of the set of candidate actions corresponds to a modification to the location of the atom, chemical bond, chemical structure portion, or reaction arrow corresponding to the selected navigation position.

In certain embodiments, the set of candidate actions comprise one or more members selected from the group consisting of (i) adding a carbon ring, (ii) adding a chemical bond, (iii) adding an atom, (iv) adding a text entry, (v) changing a bond angle, (vi) changing a chemical bond type (e.g., between a single, double, or triple bond), (vii) rotating a chemical bond by an angle, and (viii) flipping a chemical bond around an axis.

In certain embodiments, the method comprises updating the set of candidate actions in real-time based on the selected navigation position.

In certain embodiments, when the navigation position corresponds to the location of an atom, the set of candidate actions comprise one or more members selected from the group consisting of (i) adding a carbon ring, (ii) adding a chemical bond, (iii) adding an atom, and (iv) adding a text entry.

In certain embodiments, when the navigation position corresponds to the location of a first chemical bond, the set of candidate actions comprise one or more members selected from the group consisting of (i) adding a carbon ring, (ii) adding a second chemical bond, (iii) adding an atom, (iv) adding a text entry, (v) changing an angle of the first chemical bond, (vi) changing a bond type of the first chemical bond (e.g., between a single, double, or triple bond, e.g., between a bold bond, a wavy bond, a dashed bond, a hashed wedged bond, and a wedged bond), (vii) rotating the first chemical bond by an angle, and (viii) flipping the first chemical bond around an axis.

In certain embodiments, when the navigation position corresponds to the location of a chemical structure portion, the set of candidate actions comprise one or more members selected from the group consisting of (i) selecting a different chemical structure portion, (ii) creating a reaction, (iii) duplicating the chemical structure portion, and (iv) joining the chemical structure portion to a different chemical structure portion at a bond or atom.

In certain embodiments, when the navigation position corresponds to the location of a reaction arrow, the set of candidate actions comprise one or more members selected from the group consisting of (i) adding reaction conditions and (ii) adding associated reagents and/or reactants.

In certain embodiments, each action of the set of candidate actions is derived from an evaluation of whether the action is chemically feasible.

In certain embodiments, each action of the set of candidate actions is derived from an evaluation of whether it is chemically feasible to (i) append, to an atom, bond, or chemical structure portion associated with the selected navigation position, a chemical structure associated with the action or (ii) replace or partially replace the atom, bond, or chemical structure portion associated with the selected navigation position with the atom, bond, or chemical structure portion structure associated with the action.

In certain embodiments, the method comprises arranging the set of candidate actions in a ranked order for rendering on the second graphical display.

In certain embodiments, the method comprises arranging the set of candidate actions in a ranked order and display a selection of the top ranked candidate actions on the second graphical display as predictive action icons (e.g., predictive action buttons).

In certain embodiments, each action of the set of candidate actions is derived from a document using a parsing technique.

In certain embodiments, the method comprises identifying a plurality of predictive actions, wherein each predictive action of the plurality of predictive actions is derived from a database and/or based on a frequency of use by one or more users; and displaying one or more predictive actions from the plurality in or above the selection control panel of the context-aware virtual keyboard on the second graphical display.

In certain embodiments, three or fewer predictive actions are displayed in or above the selection control panel of the context-aware virtual keyboard on the second graphical display.

In certain embodiments, the method comprises displaying a chemical structure associated with one of the plurality of predictive actions as being appended to the in-progress chemical structure.

In certain embodiments, the navigation control panel comprises a plurality of navigation icons (e.g., navigation buttons).

In certain embodiments, each of the plurality of navigation icons has a display area in a range from about 30 to about 50 pixels.

In certain embodiments, the navigation control panel comprises directional arrows or a "navigation wheel" for selecting the navigation position.

In certain embodiments, the navigation control panel comprises ancillary action buttons for one or more the actions selected from the group consisting of (i) deleting an atom, bond, or portion of the chemical structure corresponding to the navigation position, (ii) adding a reaction, (iii) undoing a previous action, (iv) redoing a previous action, and (v) selecting an atom, bond, or portion of the chemical structure.

In certain embodiments, the navigation control panel comprises 12 icons or less.

In certain embodiments, the set of candidate actions are displayed as a plurality of action icons (e.g., action buttons) in the selection control panel.

In certain embodiments, each of the plurality of action icons (e.g., action buttons) has a display area in a range from about 30 to about 50 pixels.

In certain embodiments, the selection control panel comprises 20 action icons (e.g., action buttons) or less.

In certain embodiments, the selection control panel displays 20 icons or less on each of a plurality of selection screens, and comprises a scroll icon for switching between the selection screens.

In certain embodiments, the first graphical display has a display region of about 1400 cm² or greater in area (e.g., a 22 inch computer monitor has dimensions of about 47 cm×30 cm or a display region of about 1410 cm² in area)].

In certain embodiments, the second graphical display has a display region of about 150 cm² [e.g., wherein the second graphical display is a display of a tablet computer with a display region of about 150 cm² or less in area (e.g., an Apple® iPhone X® by Apple Inc. of Cupertino, Calif. has a display with dimensions of about 140 mm×70 mm or a display region of about 100 cm² in area)] or less in area.

In certain embodiments, the first graphical display is a computer monitor, a television, or a projected image.

In certain embodiments, the second graphical display is a touchscreen display of a mobile phone or a tablet computer.

BRIEF DESCRIPTION OF THE DRAWINGS

The foregoing and other objects, aspects, features, and advantages of the invention will become more apparent and may be better understood by referring to the following description taken in conjunction with the accompanying drawings, in which:

FIG. 4 is an illustration of the identification of predictive action buttons using a chemical intelligence module, according to an illustrative example;

FIG. 5A is a method for editing a graphical representation of a chemical structure using a context-aware virtual keyboard, according to an illustrative example;

FIG. 5B is a method for editing a graphical representation of a chemical structure using a dual-display context-aware virtual keyboard, according to an illustrative example;

Figure 9A:
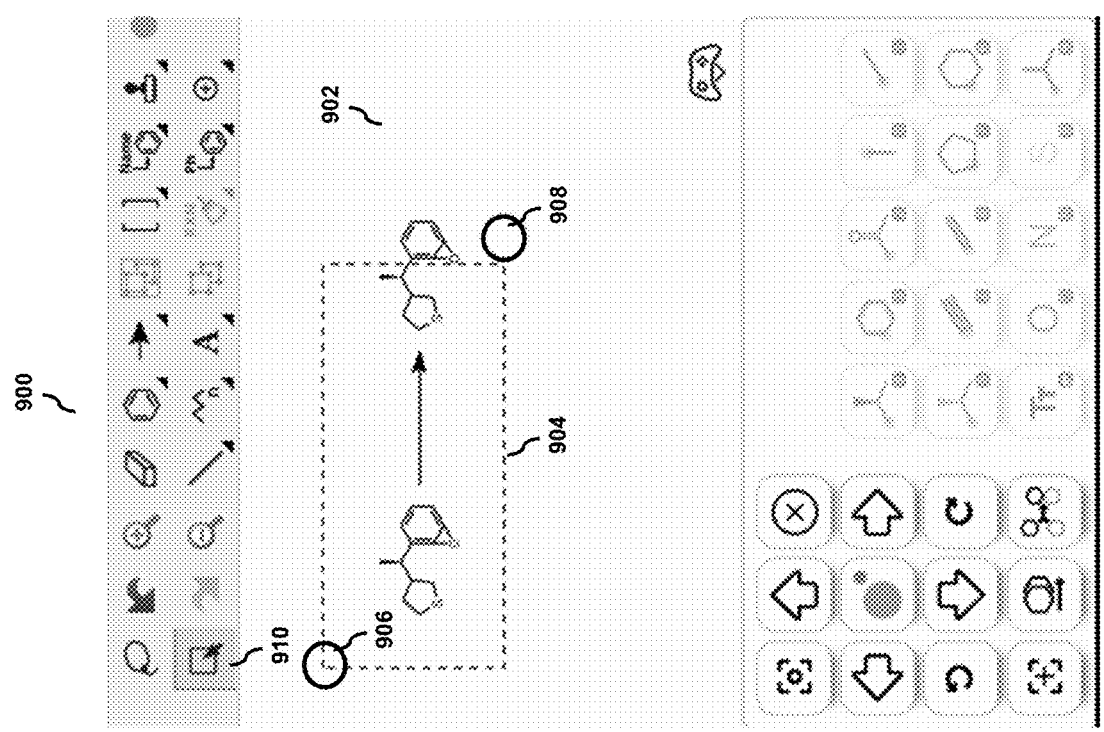
Figure 9B:
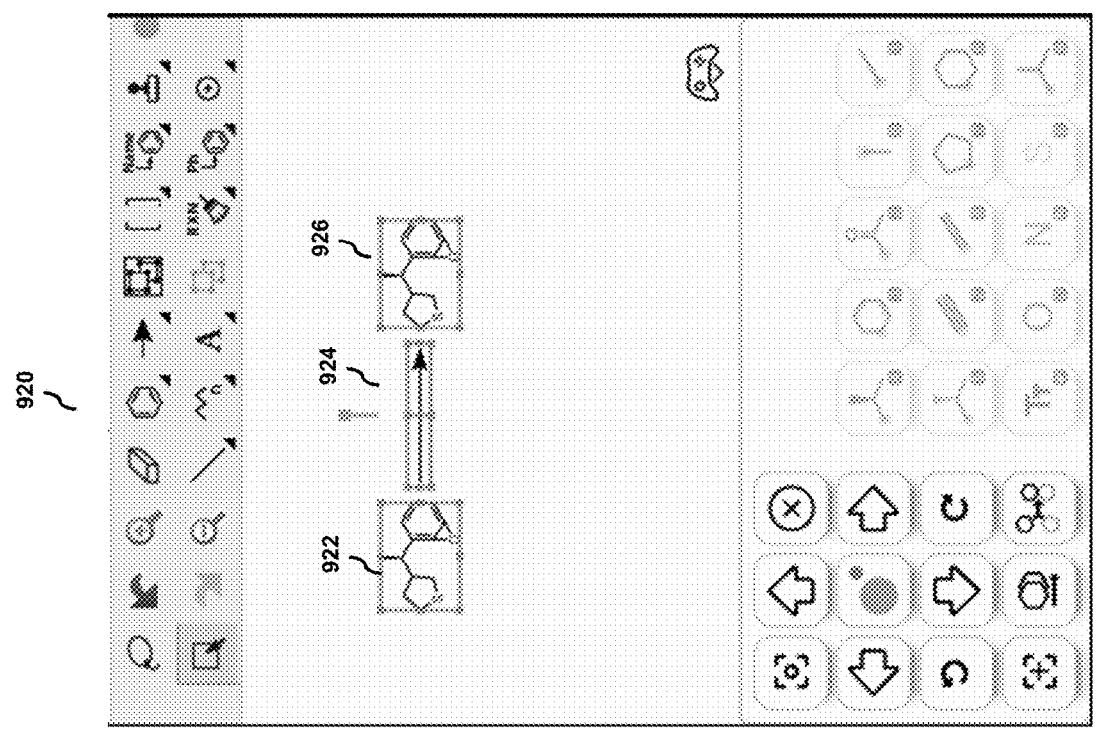
Figure 10A:
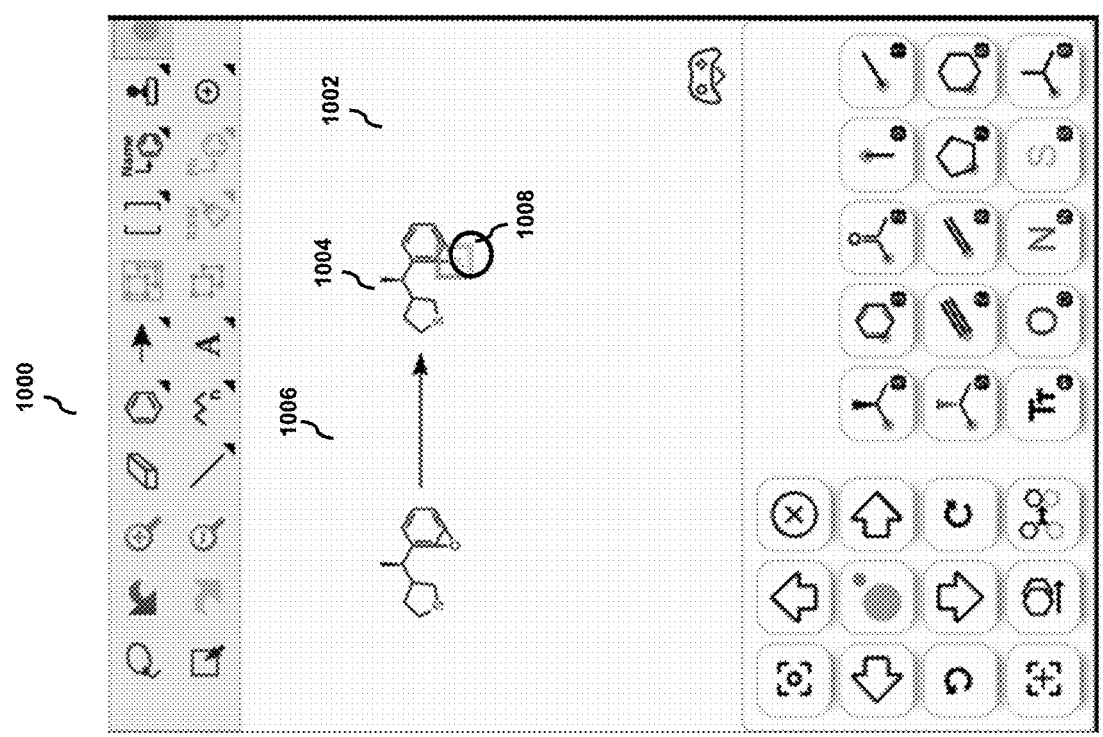
Figure 10B:
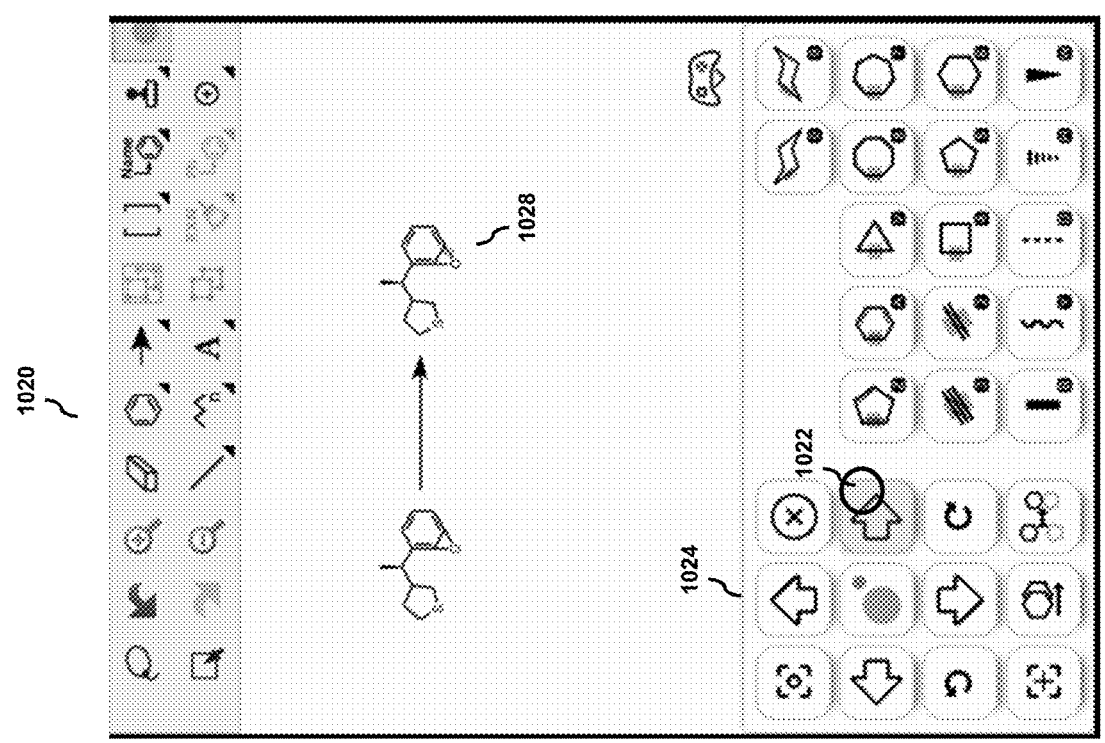
Figure 10C:
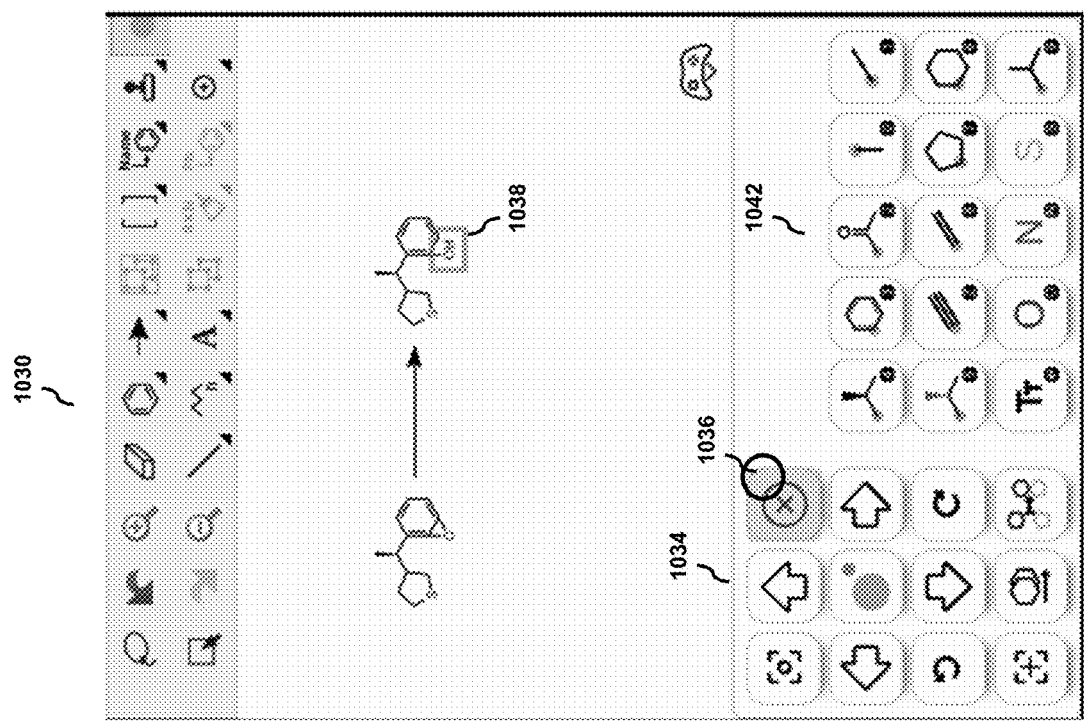
Figure 11:
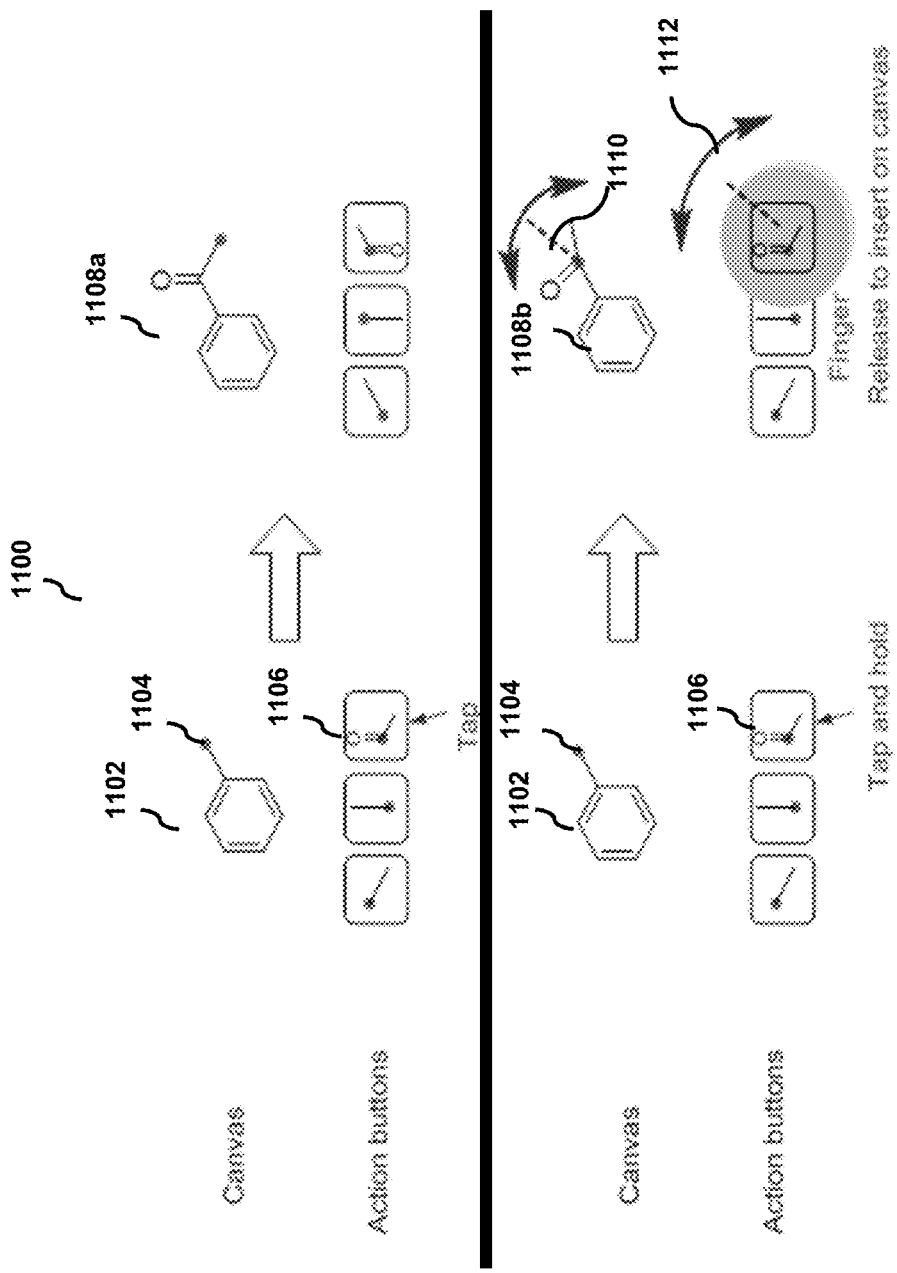
Figure 12:
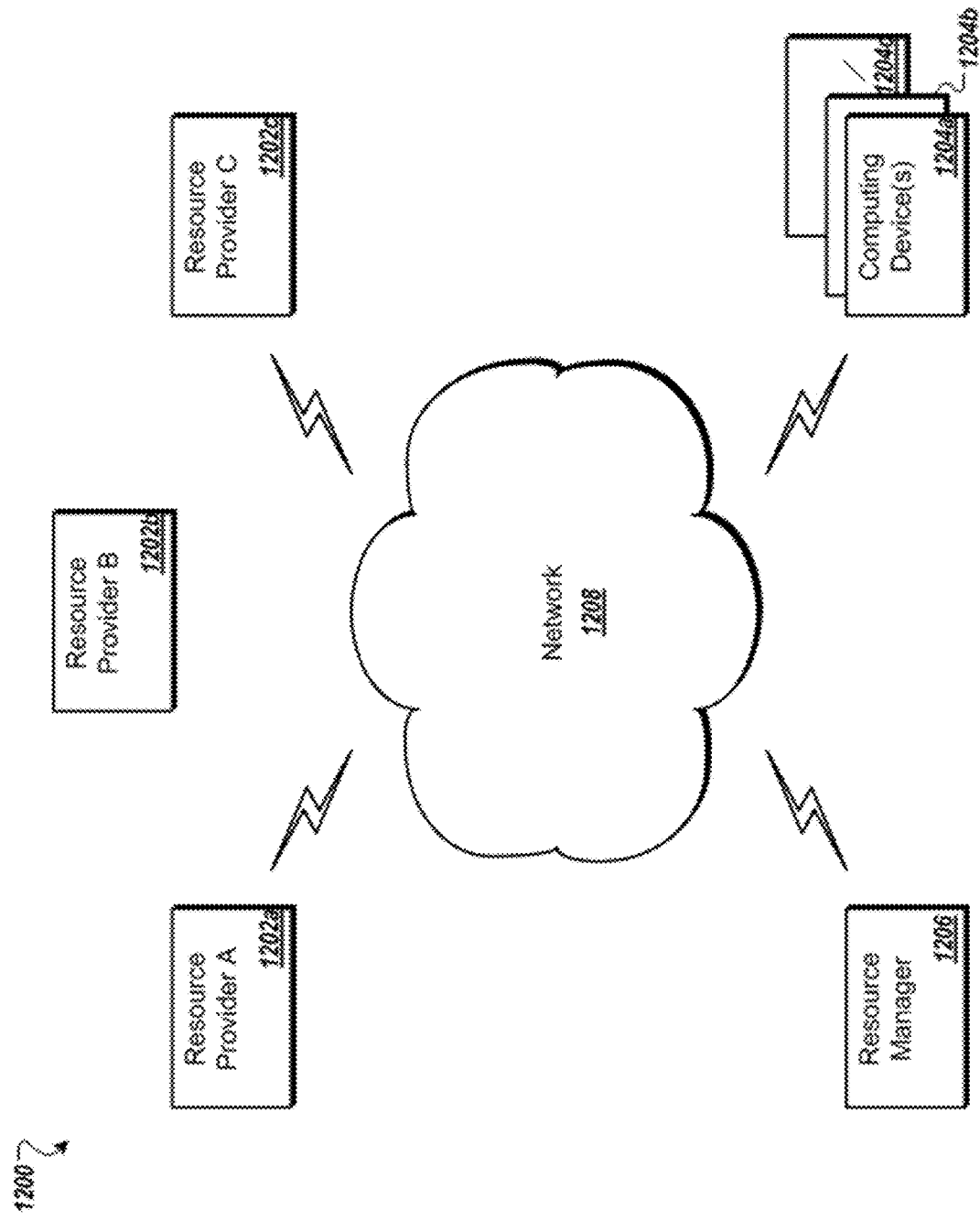
Figure 13:
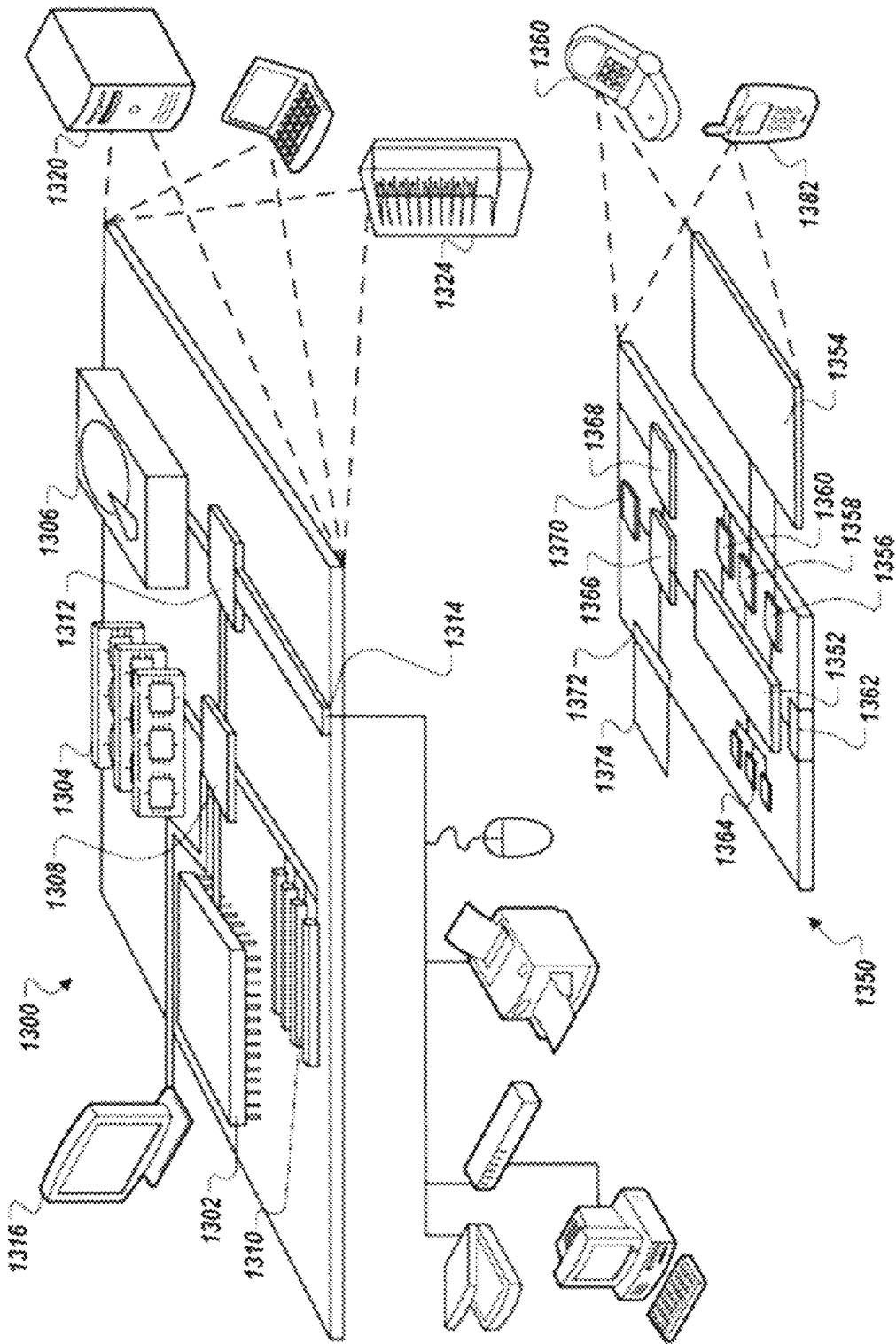

FIB. 8 shows a screenshot of a context-aware virtual keyboard acquired while a user repositioned a representation of a chemical reaction, according to an illustrative embodiment;

FIG. 9A and FIG. 9B show screenshots of a context-aware virtual keyboard acquired while a user selected multiple portions of a representation of a chemical reaction, according to an illustrative embodiment;

FIG. 10A, FIG. 10B, and FIG. 10C show screenshots of a context-aware virtual keyboard acquired while a user navigated to a bond and deleted the bond from a representation of a chemical structure, according to an illustrative embodiment;

FIG. 11 shows an illustrative example of a method for editing a representation of a chemical structure using a dynamic action button;

FIG. 12 is a schematic diagram of an example system for drawing or editing chemical structures;

FIG. 13 is a block diagram of an example computing device and an example mobile computing device; and FIG. 14 is a schematic diagram of an example system for drawing or editing chemical structures.

The features and advantages of the present disclosure will become more apparent from the detailed description set forth below when taken in conjunction with the drawing, in which like reference characters identify corresponding elements throughout. In the drawing, like reference numbers generally indicate identical, functionally similar, and/or structurally similar elements.

DESCRIPTION

It is contemplated that apparatus, systems, and methods of the claimed invention encompass variations and adaptations developed using information from the embodiments described herein. Adaptation and/or modification of the apparatus, systems, and methods described herein may be performed by those of ordinary skill in the relevant art.

Throughout the description, where apparatus and systems are described as having, including, or comprising specific components, or where processes and methods are described as having, including, or comprising specific steps, it is contemplated that, additionally, there are apparatus and systems of the present invention that consist essentially of, or consist of, the recited components, and that there are processes and methods according to the present invention that consist essentially of, or consist of, the recited processing steps.

It should be understood that the order of steps or order for performing certain actions is immaterial so long as the invention remains operable. Moreover, two or more steps or actions may be conducted simultaneously.

The mention herein of any publication is not an admission that the publication serves as prior art with respect to any of the claims presented herein. The Background section is presented for purposes of clarity and is not meant as a description of prior art with respect to any claim.

Documents are incorporated herein by reference as noted. Where there is any discrepancy in the meaning of a particular term, the meaning provided in the Definition section above is controlling.

Headers are provided for the convenience of the reader—the presence and/or placement of a header is not intended to limit the scope of the subject matter described herein.

In general, in various embodiments, the present invention pertains to apparatus, systems, and methods for drawing chemical structures on a computing device. The computing device may be, for example, a personal computer, a workstation, a tablet computer (e.g., an Apple® IPad® by Apple Inc. of Cupertino, Calif.), or a mobile phone (e.g., an Apple® IPhone® by Apple Inc. of Cupertino, Calif.).

The systems and methods described herein can be used to create graphical representations of chemical structures (e.g., molecules) and chemical reactions for publications or reports. The systems and methods described herein can also be used to create graphical representations of chemical structures (e.g., molecules) and chemical reactions for use in search engines, e.g., to search for other chemical structure representations with similar and/or associated characteristics. For example, a graphical representation of a chemical structure may be used to search a database of predefined chemical structures to identify similar known molecules and/or known reactions related to the chemical structure.

Figure 1:
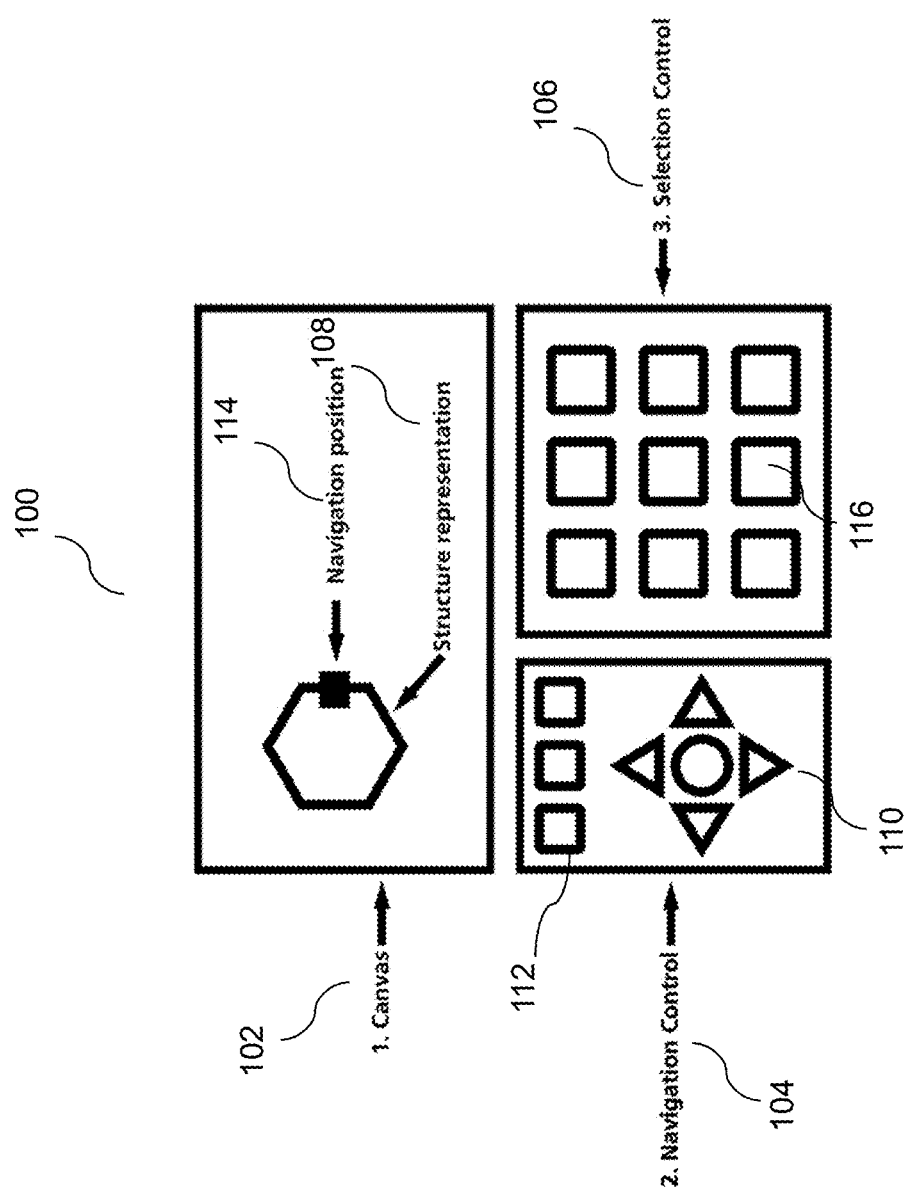
FIG. 1 is a diagram of a context-aware virtual keyboard for drawing and/or editing representations of chemical structures, according to an illustrative example.

FIG. 1 shows a diagram of a context-aware virtual keyboard 100 for drawing and/or editing representations of chemical structures, according to an illustrative embodiment. The context-aware virtual keyboard includes a canvas panel 102, a navigation control panel 104, and a selection control panel 106. Canvas panel 102 provides a space for displaying an in-progress chemical structure representation 108. Navigation control panel 104 and selection control panel 106 allow a user to create and/or modify chemical structure representation 108 on a touchscreen device without the finger and/or hand of the user obstructing his/her view of chemical structure representation 108. Navigation control panel 104 includes navigation controls 110 and action buttons 112. As used herein, the term "button" generally refers to an icon displayed on a touchscreen device; a user may touch (e.g., tap or press with a finger) the touchscreen device at the location of a button to initiate the corresponding action or response from the context-aware virtual keyboard. The navigation controls allow a user to adjust navigation position 114 to different locations on the chemical structure representation 108. The navigation position 114 is at the location of a carbon-carbon bond in chemical structure representation 108. Action buttons 112 allow a user to modify chemical structure representation 108. For example, action buttons 112 may allow a user to delete a selected atom or bond from chemical structure 108 or create a representation of a chemical reaction (e.g., by inserting a reaction arrow in canvas panel 102 and/or copying all or a portion of chemical structure representation 108 to the right of the reaction arrow).

Still referring to FIG. 1, selection control 106 includes a set of context-based candidate actions for modifying the chemical structure representation 108 presented in canvas panel 102. For example, the candidate actions may include adding (e.g., sprouting from a selected atom or fusing to a selected bond) a chemical structure fragment (e.g., a carbon chain, e.g., a carbon ring) or a chemical bond (e.g., a single bond, e.g. a double bond, e.g., a triple bond) at the navigation position. As used herein, the term "chemical structure fragment" refers to a portion of a chemical structure representation. These candidate actions are presented to the user as action buttons (e.g., action icons) 116 and are continuously updated based on navigation position 114. For example, a different set of action buttons are presented when navigation position 114 corresponds to the location of an atom than when navigation position 114 corresponds to the location of a bond. Table 1 shows examples of candidate actions which may be presented in the selection control panel based on whether the selected navigation position corresponds to the position of a chemical bond or an atom.

TABLE 1

Example actions presented in selection control panel based on the navigation position

| Navigation position | Example Actions |
| --- | --- |
| Atom | Sprout a bond or chemical structure fragment, change angle of adjacent bond(s), add query attributes |
| Chemical Bond | Change bond type, fuse a chemical structure fragment to the bond, add query attributes, change bond angle, flip bond around an axis, rotate bond |

TABLE 1-continued

Example actions presented in selection control panel based on the navigation position

| Navigation position | Example Actions |
| --- | --- |
| Chemical Structure | Select entire structure, create reaction from structure, clone, join to another structure through atom or bond |
| Reaction Arrow | Add reaction conditions in a structured manner, associate reactants/reagents. |

The set of action buttons may be based on chemical rules. For example, action buttons may correspond to modifications to in-progress chemical structure representation 108 that are feasible based on established rules of chemistry. For example, the context-aware virtual keyboard may determine whether or not a given edit would result in a structure that is chemically feasible and may limit the set of candidate actions displayed as action buttons 116 to only those resulting in feasible chemical structures.

In certain embodiments, the action buttons are toggled based on the selected navigation positions. For example, when the navigation position corresponds to the location of an atom, the action buttons displayed in the selection control panel may allow a user to sprout a bond or chemical structure fragment from the selected atom and change the angle of chemical bond(s) adjacent to the selected atom.

Action buttons may also be presented that allow a user to add query attributes to the selected atom. For example, a query attribute may include additional information about an atom, bond, chemical structure portion, or reaction arrow in a representation of a chemical structure or chemical reaction. For example, query attributes may include a searchable text string that allows a user to rapidly find the atom at a later time using a search query. For example, if a user wishes to identify a selected atom as a generic atom, the query attribute may include a text string such as "any atom of this sort". A query attribute can include information about chemical transformations associated with an atom, bond, or portion of the chemical structure representation (e.g., the query attribute may include the text string "this atom is not modified in a reaction"). A query attribute may include information about the type of atom or other properties of an atom (e.g., the query attribute may include the text string "this atom is a member of the carbon group of the periodic table of elements" and/or the text string "this atom is bonded to two or more other atoms").

In certain embodiments, query attributes allow users to more quickly and efficiently retrieve saved graphical representations of chemical structures or chemical reactions. For example, the saved representations may have been created at an earlier time and saved in a memory of a computing device. For example, responsive to a search request, saved chemical structures and/or chemical reactions with query attributes that match or are similar to the search request may be retrieved from the memory. The number of retrieved representations may be limited in number such that, for example, a user may more efficiently locate a chemical structure of interest. For example, responsive to a search request, a subset of the saved chemical structure representations may be retrieved. The subset may, for example, include less than 100, less than 50, or less than 10 chemical structure representations.

When the navigation position corresponds to the location of a chemical bond, the action buttons displayed in the selection control panel may, for example, allow a user to change the type of the selected bond (e.g., single, double or triple bond), fuse a chemical structure fragment to the selected bond, change the angle of the selected bond, flip the selected bond around a vertical or horizontal axis, rotate the bond by an arbitrary or predetermined angle (e.g.,) 180°, and add query attributes to the selected bond (e.g., similar to those described above for a selected atom). For example, when the navigation position corresponds to the location of a chemical structure, action buttons may allow a user to select the entire structure, create a representation of a chemical reaction based on the selected structure, clone the selected structure, and join the selected chemical structure to another structure, for example, via an atom or chemical bond. For example, when the navigation position corresponds to the location of a chemical reaction arrow, action buttons may allow a user to intuitively add text labels related to, e.g., reaction conditions and/or associated reactants/reagents.

In certain embodiments, the action buttons are "grayed out" (e.g., as shown in selection control panel 706 of FIG. 7A) when the user is performing an operation where action buttons are not relevant. For example, action buttons may not be required when an entire chemical structure representation is selected and/or when a "copy/paste" or "duplication" command is being executed.

Figure 2A:
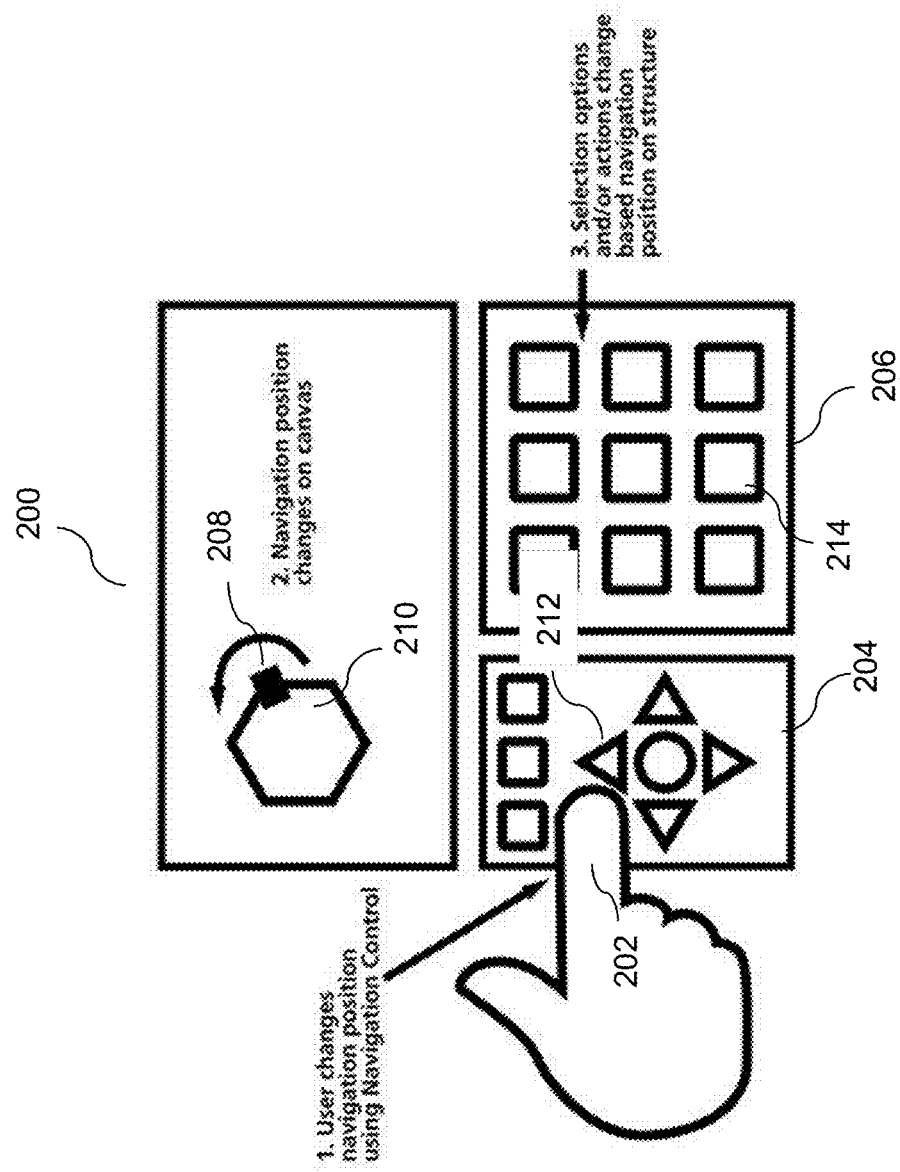
FIG. 2A and FIG. 2B show illustrations of the use of the navigation control panel of a context-aware virtual keyboard for drawing and/or editing graphical representations of chemical structures, according to an illustrative example.

FIG. 2A shows an illustrative example of the use of the navigation control panel 204 of context-aware virtual keyboard 200. In this illustrative example, a user changes the navigation position 208 by contacting their finger 202 to the "up" directional arrow 212 (Step 1 of FIG. 2A).

Upon selection of the "up" directional arrow 212 navigation position 108 (FIG. 1) shifts to navigation position 208 on chemical structure representation 210 (Step 2 of FIG. 2A). After switching to navigation position 208, a different set of action buttons 214 are presented in selection control panel 206 (Step 3 of FIG. 2A). Action buttons 214 correspond to possible/likely actions for modifying the carbon atom at navigation position 208. For example, possible actions include sprouting a chemical bond or sprouting a chemical structure fragment from the selected atom.

Figure 2B:
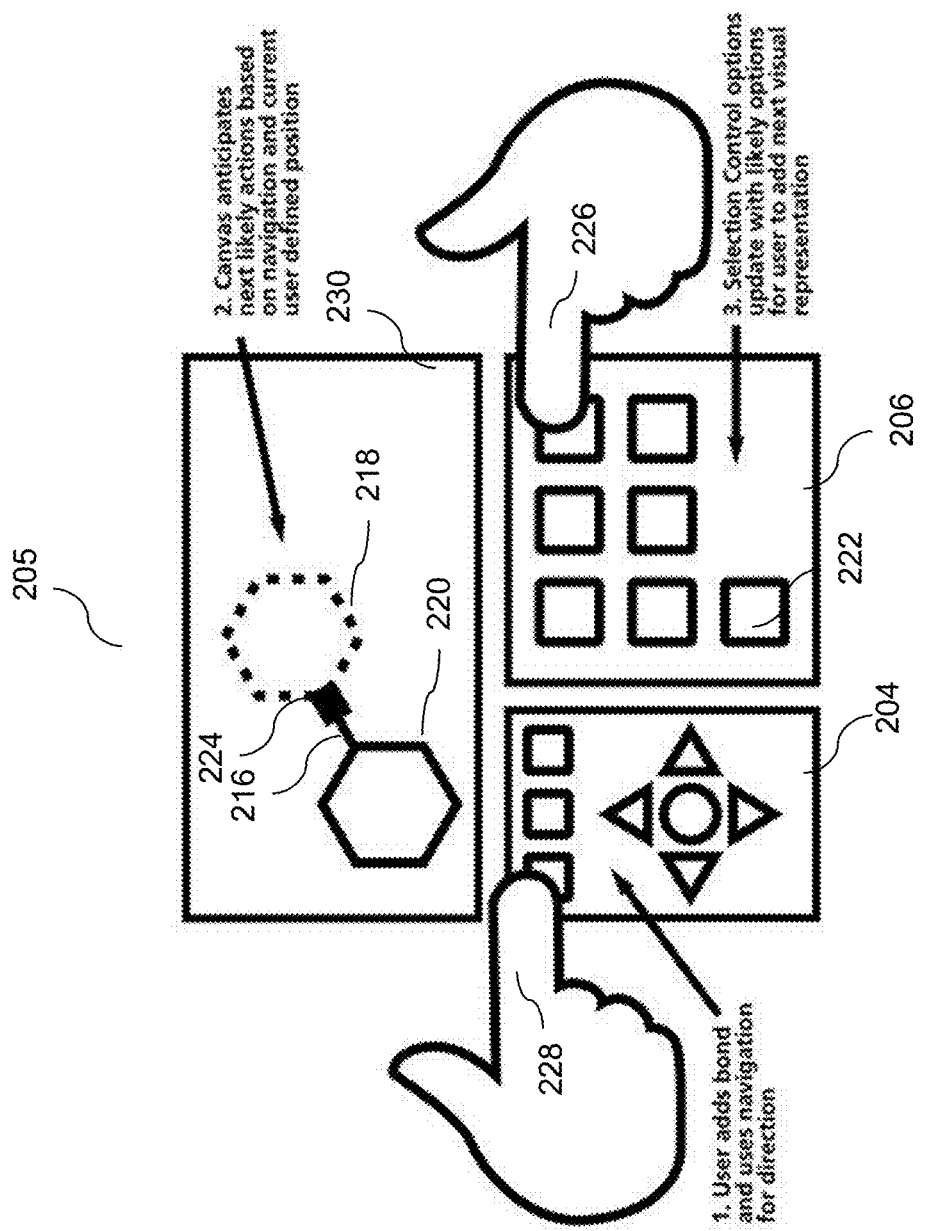

FIG. 2B shows an illustrative example of context-aware virtual keyboard 205 after a chemical bond 216 is added to the carbon atom corresponding to navigation position 208 in FIG. 2A. A user adds chemical bond 216 by selecting (with finger 226) the corresponding action button from selection panel 206, and the user modifies the direction of the chemical bond (with finger 228) using navigation control panel 204 (Step 1 of FIG. 2B). After chemical bond 216 is added to chemical structure representation 220, the set of action icons 222 presented in selection control panel 206 is updated to correspond to the modification of new navigation position 224 at the end of chemical bond 224. For example, action buttons 222 may correspond to fusing an atom or chemical structure (e.g., a chemical fragment) to the end of chemical bond 216.

In certain embodiments, the canvas anticipates likely actions based on the navigation position and/or other properties of the user interface (e.g., Step 2 of FIG. 2B). In some embodiments, the history of edits made by a user or a group of users may determine likely additions to a chemical structure representation. In other embodiments, likely modifications may be obtained from one or more files, documents, and/or databases. For example, a user may indicate that an in-progress chemical structure drawing is associated with a document that includes a set of predefined chemical structure representations. For example, referring to the illustrative example of FIG. 2B, the addition of carbon ring 218 is presented as an anticipated action for modifying chemical structure representation 220 in canvas panel 230 (e.g., as a dashed-line structure) (Step 2 of FIG. 2B).

Figure 3A:
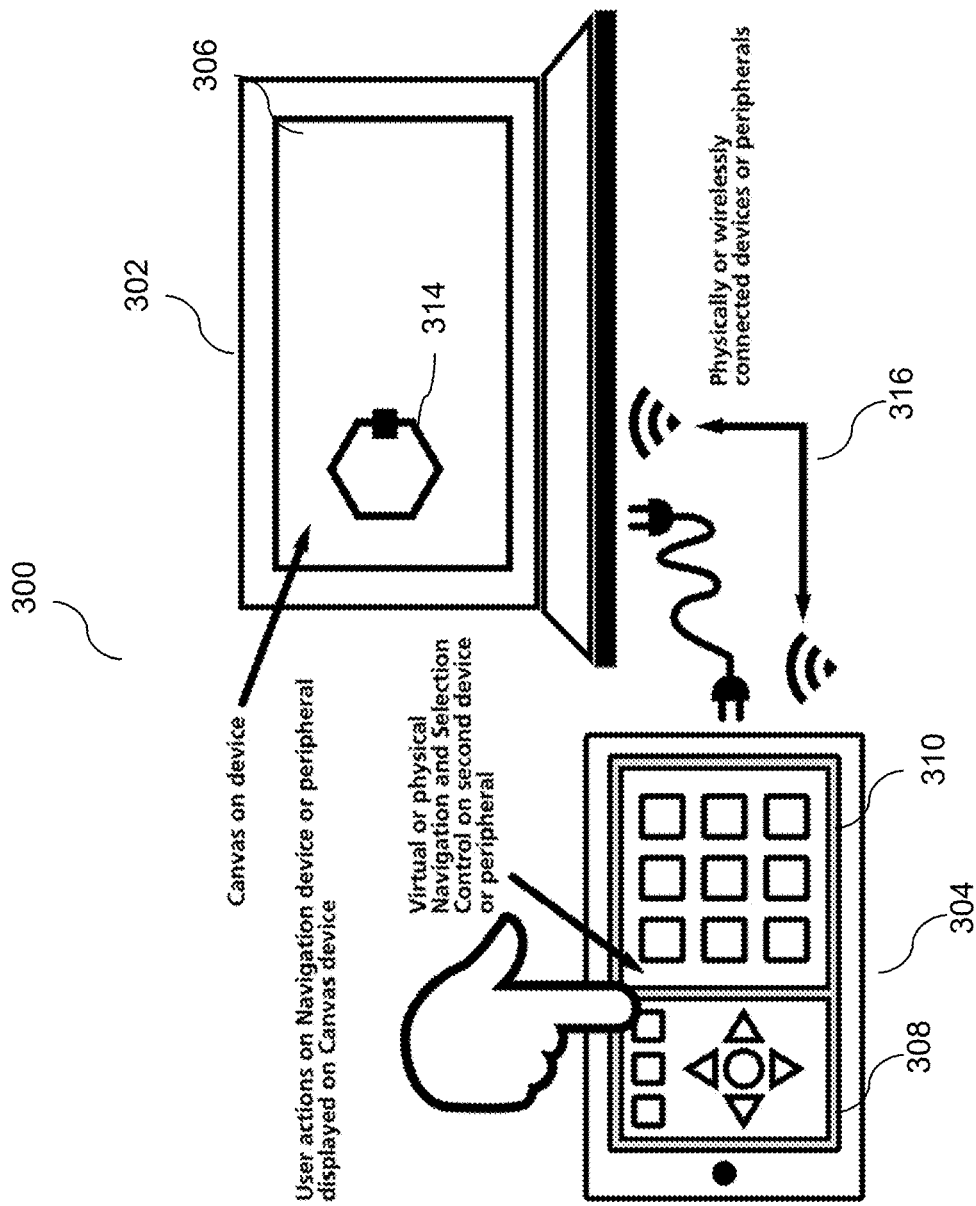
FIG. 3A is an illustration of the use of a dual-display context-aware virtual keyboard for drawing and/or editing graphical representations of chemical structures, according to an illustrative example.

In certain embodiments, the context-aware virtual keyboard is presented on two graphical displays as a dual-display context-aware virtual keyboard. FIG. 3A shows an illustrative example of the use of a dual-display context-aware virtual keyboard 300. The canvas panel 306 is presented on a relatively large display (e.g., with a display area of 1400 cm$^2$ or larger) 302 and the navigation control panel 308 and selection control panel 310 are displayed on a smaller touchscreen device 304 (e.g., a tablet computer or mobile phone device). This dual-display setup allows a user to intuitively and rapidly operate the navigation and selection control panels using a handheld device, while the in-progress chemical structure representation is displayed on a larger display. Touchscreen device 304 and display 302 can be operatively connected through a wire (e.g., via USB or Ethernet) or wirelessly (e.g., via wireless Ethernet or BLUETOOTH®) (316). A user may then proceed to selects icons displayed on device 304 to update chemical structure representation 314 which is presented on display 302.

In certain embodiments, the canvas panel of the context-aware virtual keyboard fills greater than 70%, 80%, 90%, more of the graphical display. For example, the navigation and selection control panels may be overlaid on the canvas control panel of the context-aware virtual keyboard. This overlaid format allows the context-aware virtual keyboard to fit more effectively on relatively small graphical displays (e.g., the graphical displays of mobile phone devices or tablet computers).

Figure 3B:
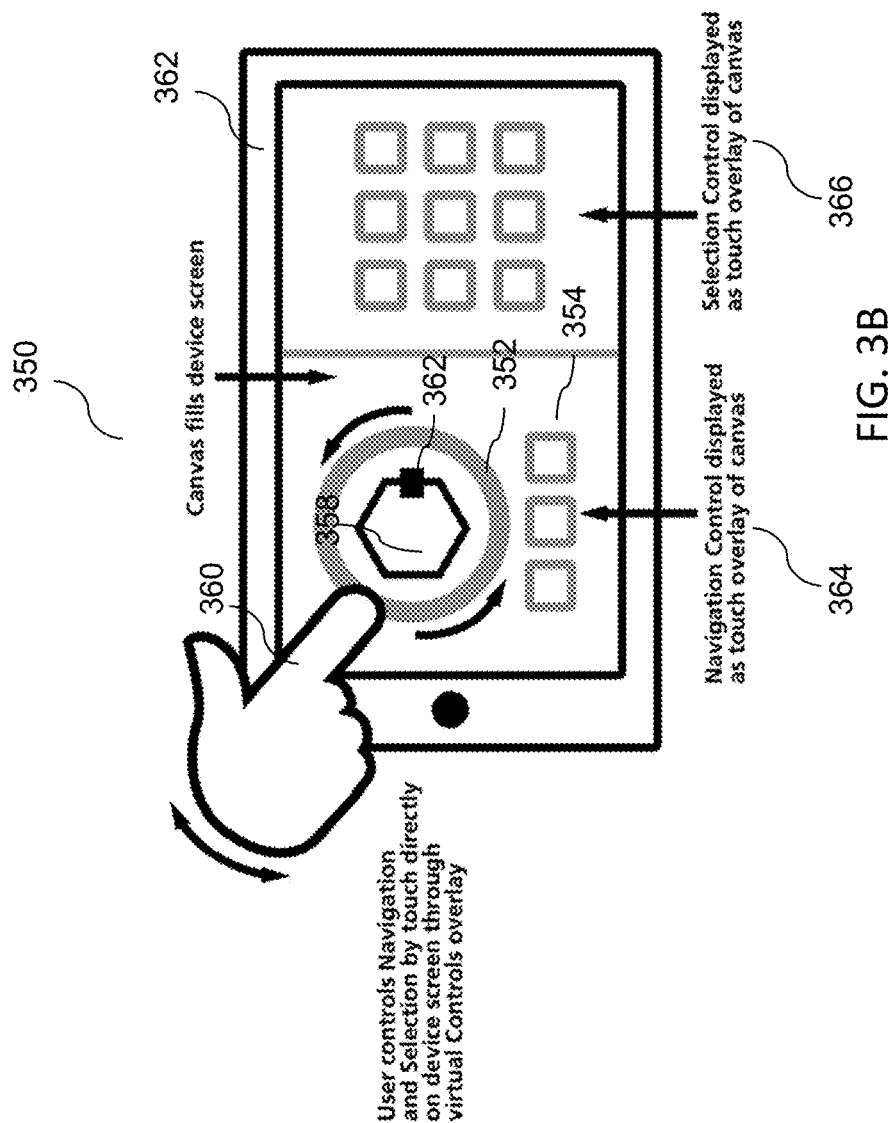
FIG. 3B is an illustration of the use of a context-aware virtual keyboard with the navigation control panel and selection control panel overlaid on the canvas panel for drawing and/or editing graphical representations of chemical structures, according to an illustrative example.

FIG. 3B shows an illustrative example of the use of a context-aware virtual keyboard 350 in which the canvas panel fills the entire display of device 362. The navigation control panel 364 and selection control panel 366 are overlaid on the canvas panel. In this illustrative example, the navigation control panel 364 is overlaid on the chemical structure representation 358. The navigation control panel 364 includes action buttons 354 and a "navigation wheel" 352 for modifying the navigation position 362 on chemical structure representation 358. The action buttons 354 are analogous to action buttons 112 of FIG. 1. Navigation wheel 352 provides directional functionality similar to that provided by directional arrows 110 shown in FIG. 1.

For example, to choose a navigation position using navigation wheel 352, a user may sweep a finger 360 on the surface of the display of device 362 corresponding to the position of navigation wheel 352. The user operates navigation wheel 352 in a manner similar to rotating a wheel, motion of finger 360 over the navigation wheel 352 corresponds to movement of the navigation position 362 between, for example, different atoms and/or chemical bonds on chemical structure representation 358. The navigation wheel 352 may, for example, require less space on the display 362 while providing an intuitive control of the navigation position 362.

In certain embodiments, predictive actions for modifying an in-progress chemical structure representation may also be determined by a chemical intelligence module. The chemical intelligence module identifies predictive actions from document(s) of a user, the local computing environment and/or device of the user, and/or other connected systems (e.g., systems connected locally or remotely, e.g., via a network or via an internet-based service). For example, a set of documents, a set of files, and/or one or more reference libraries containing predefined sets of chemical structure representations may be parsed to identify likely actions. The set of documents, set of files, and/or one or more reference libraries may be available on the computing device of a user (e.g., stored locally on the computing device of the user) or accessed via a connected system such as a shared database accessed over a network or an internet-based service.

The chemical intelligence module may employ machine learning, pattern recognition, and/or artificial intelligence techniques to determine common structural patterns in these predefined sets of chemical structure representations. For example, keypoint matching, perceptual hashing, and/or histogram matching may be used to train the chemical intelligence module using training data stored in reference dictionaries. Reference dictionaries may include, for example, chemical structure representations previously drawn by a user, known chemical structures, and libraries of structures defined by third party organizations.

The chemical intelligence module may also identify predictive actions based on a history of previous actions. This identification can be performed in a continuous manner, and predictive actions identified using the chemical intelligence module may be associated with a user, a group of users, a project, and/or a class of chemical structures. For example, the chemical intelligence module may identify a set of likely actions associated with a specific user, a specific group of users (e.g., a research group or company working on a particular class of chemical structures or in a specific subfield of chemistry), or a specific chemical structure type. In certain implementations, predictive actions may be identified by receiving a chemical structure as a "favorite" from a user, for example, through a user interface capture feature. For example, a user may enter or select one or more chemical structures (or one or more portions of a chemical structure) that the user anticipates drawing frequently.

In certain implementations, a collection of chemical structures are received and reviewed by the chemical intelligence module to identify predictive actions. For example, chemical structure representations may be captured in a registration system (e.g., registering structures to associate with a software license or user identification within a system including a chemical formula drawing program with a context-aware virtual keyboard), culled from public data sets, read from a chemical structure database such as the Available Chemicals Exchange (ACX) maintained by PerkinElmer of Waltham, Mass., captured as new chemical structures from an electronic lab notebook (ELN) system, or identified through optical character recognition (OCR) systems.

In certain embodiments, the predictive actions identified are displayed as predictive action buttons. For example, in some implementations, icons for the three most likely functional groups to be added to the current navigation position may be displayed as predictive action buttons. Predictive action buttons can also correspond to actions for modifying other objects such as a selected portion of a chemical structure representation, a reaction arrow, or both.

FIG. 4 is an illustrative example 400 of the identification of predictive action buttons 412 and 416 using a chemical intelligence module. The chemical intelligence module identifies structural patterns in predefined chemical structure representations 402, 404, 406, and 408. When navigation position 410 (corresponding to the position of a carbon atom) is selected, predictive action buttons 412 are displayed above navigation control panel 418 and selection control panel 420. When navigation position 414 (corresponding to the position of a chemical bond in a carbon ring) is selected, predictive action buttons 416 are displayed above navigation control panel 422 and selection control panel 424.

In certain embodiments, one or more of the action buttons (e.g., one or more of the predictive action buttons or one or more of the action buttons displayed in the selection control panel) are dynamic action buttons. A dynamic action button responds differently based on the properties of a touch-based input from a user. For example, a dynamic action button may provide different actions (e.g., corresponding to modifications of different properties of the chemical structure representation) based on whether the button is tapped once, tapped multiple times, or pressed and held.

For example, dynamic action buttons can be sensitive to the length of time a user presses the button, a frequency at which the button is tapped, and/or a motion made by a finger of a user after the button is pressed and held. In certain embodiments, a user can tap a dynamic action button to preview the result of selecting the button. The action may then be performed by tapping the button twice within a short period of time (e.g., for one second or less, e.g., double-tapping" the button) or pressing the button for a longer period of time (e.g., for one second or longer, e.g., "pressing and holding" the button). In certain embodiments, a user can "touch, hold, and drag" a dynamic action button to, for example, rotate a chemical structure representation, change the angle of an added bond or functional group, or resize structures as they are appended to an in-progress chemical structure representation. It should be understood that various other functionalities of dynamic action buttons are possible based on the properties of the device used to present the context-aware virtual keyboard. For example, dynamic action buttons, in certain embodiments, respond differently based on the amount of force applied to the screen (e.g., when the touchscreen is pressure sensitive).

FIG. 11 shows an illustrative example of a method 1100 for editing a representation of a chemical structure representation 1102 at navigation position 1104 using a dynamic action button 1106. In this illustrative example, dynamic action button 1106 functions differently when it is tapped by a user than when it is tapped and held by the user. The top row of FIG. 11 shows an illustrative example of a chemical structure representation 1108a that is created by briefly tapping dynamic action button 1106.

Still referring to FIG. 11, the bottom row shows an illustrative example of a chemical structure representation 1108b that is created by tapping and holding dynamic action button 1106. In this example, the user adjusts the angle between the carbon-oxygen double bond (C=O) and the carbon-carbon bond (C—C) of chemical structure representation 1108b using a ""touch, hold, and drag" input. The bond angle is adjusted (see dashed line 1110) based on the distance that the user drags his/her finger along the two-sided arrow 1112 shown in FIG. 11.

FIG. 5A is a flow chart of an example method 500 for creating a graphical representation of a chemical structure using a context-aware virtual keyboard. Method 500 begins with providing a graphical representation of at least a portion of a chemical structure (step 502). The graphical representation may include an in-progress chemical structure representation, a complete graphical representation of a chemical structure, a graphical representation of a chemical structure imported from a separate software application, or a graphical chemical structure representation stored in a document.

In step 504, an input is received for selecting a navigation position from the navigation control panel of the context-aware virtual keyboard. Based on the navigation position selected in step 504, a set of candidate actions are identified (step 506) and displayed (step 508) in the canvas panel of the context-aware virtual keyboard. In certain embodiments, the candidate action are displayed in a ranked order by identifying a usage count associated with each of the candidate chemical structures. An input is then received from the selection control panel of the context-aware virtual keyboard corresponding to a selection of one of the displayed candidate actions (step 510).

Upon receipt of this input, the graphical representation is updated based on the selected action in step 512. Updating the graphical representation in step 512 may include, for example, appending a chemical structure associated with the selected action to the in-progress chemical structure at an atom, bond, or chemical structure portion corresponding to the navigation position, replacing or partially replacing the atom, bond, or chemical structure portion corresponding to the navigation position in the in-progress chemical structure with the chemical structure associated with the selected action, and/or modifying an atom, bond, chemical structure portion, or reaction arrow corresponding to the navigation position in the in-progress chemical structure according to the selected action.

FIG. 5B is a flow chart of an example method 550 for creating a graphical representation of a chemical structure using a dual-display context-aware virtual keyboard. Method 550 begins with providing a graphical representation of at least a portion of a chemical structure on a first device (step 552). The graphical representation may include an in-progress chemical structure representation, a complete graphical representation of a chemical structure, a graphical representation of a chemical structure imported from a separate software application, or a graphical chemical structure representation stored in a document.

In step 554, an input is received, from a second device, for selecting a navigation position from the navigation control panel of the context-aware virtual keyboard. Based on the navigation position selected in step 554, a set of candidate actions are identified (step 556) and displayed (step 558) in the canvas panel on the second device (e.g., a handheld touchscreen device). In certain embodiments, the candidate action are displayed in a ranked order by identifying a usage count associated with each of the candidate chemical structures. An input is then received from the selection control panel of the context-aware virtual keyboard on the second device corresponding to a selection of one of the displayed candidate actions (step 560).

Upon receipt of this input, the graphical representation on the first device is updated based on the selected action in step 562. Updating the graphical representation in step 562 may include, for example, appending a chemical structure associated with the selected action to the in-progress chemical structure at an atom, bond, or chemical structure portion corresponding to the navigation position, replacing or partially replacing the atom, bond, or chemical structure portion corresponding to the navigation position in the in-progress chemical structure with the chemical structure associated with the selected action, and/or modifying an atom, bond, chemical structure portion, or reaction arrow corresponding to the navigation position in the in-progress chemical structure according to the selected action.

ILLUSTRATIVE EXAMPLES

The illustrative examples shown below include screenshots that were acquired while a user operated an embodiment of the system claimed herein. In this embodiment, the context-aware virtual keyboard was presented to the user on the touchscreen of a mobile phone device.

Example 1: Editing a Bond and an Atom Using an Embodiment of the Context-Aware Virtual Keyboard The following example demonstrates how a user can edit an illustrative chemical structure using an embodiment of the context-aware virtual keyboard described herein.

Figure 6A:
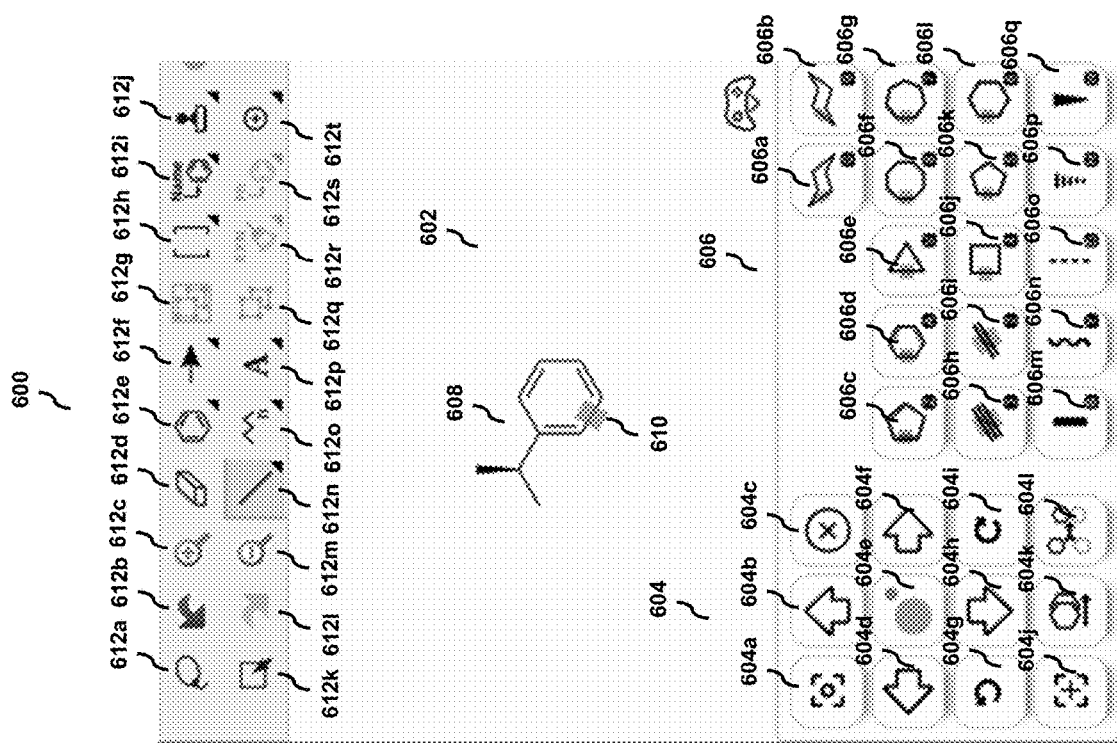
FIG. 6A, FIG. 6B, FIG. 6C, and FIG. 6D show screenshots of a context-aware virtual keyboard acquired while a user edited a graphical representation of a chemical structure, according to an illustrative embodiment.

FIG. 6A shows a screenshot 600 of an example context-aware virtual keyboard used to edit a graphical representation of a chemical structure. Screenshot 600 includes a canvas panel 602, a navigation control panel 604, and a selection control panel 606. The menu above the canvas panel includes a lasso icon (e.g., for selecting a portion of a chemical structure representation) 612a, an undo icon 612b, a zoom-in icon 612c, an eraser icon 612d, a carbon ring creation icon 612e, a reaction arrow icon 612f, an integral grouping icon 612g, a bracket icon 612h, a name-to-structure icon 612i, a template icon 612j, a marquee icon 612k, a redo icon 612l, a zoom-out icon 612m, a bond drawing icon 612n, a carbon chain drawing icon 612o, a text adding icon 612p, a grouping icon 612q, a reaction clean-up icon 612r, a label expansion icon 612s, and a charge modifying icon 612t.

The navigation control panel 604 includes icons for performing navigation and movement actions. Navigation control panel 604 includes an object selection icon 604a, an up navigational arrow icon 604b, a delete icon 604c, a left navigational arrow icon 604d, a navigation position selection icon 604e, a right navigational arrow icon 604f, an undo navigation icon 604g, a down navigational arrow icon 604h, a redo navigation icon 604i, an additive selection icon 604j, a reaction creation icon 604k, and a dual reaction creation icon 604l. Upon selecting the navigation position selection icon 604e, a user may manually select a navigation position on the in-progress chemical structure 608. The user may then adjust (e.g., fine tune) the navigation position using the navigational arrow icons (604b, 604d, 604f, and 604k). For example, the navigational icons allow a user to select a desired navigation position that is difficult to select manually on a touchscreen interface (e.g., because the display area of the touchscreen of a mobile phone device may be small). Responsive to the selection of reaction creation icon 604k, a reaction arrow is inserted to the right of the selected object(s) and a copy of the selected object(s) is inserted to the right of this arrow. Dual reaction icon 604l creates a reaction arrow to the right of selected object(s) and inserts a probable reaction product of the selected object(s) to the right of this reaction arrow.

Canvas panel 602 includes a graphical representation of an in-progress chemical structure 608. In this illustrative example, a bond was recently added to chemical structure 608. Navigation position 610 automatically appeared on the chemical structure at this most recently edited location. Since navigation position 610 is located on a bond, selection control panel 606 displays action buttons for editing this bond. Each button includes a visual representation of what will be added at the location of navigation position 610.

Selection control panel 606 includes action buttons for fusing a chair cyclohexane (1) to the selected bond (icon 606a), fusing a chair cyclohexane (2) to the selected bond (icon 606b), fusing a cyclopentadiene to the selected bond (icon 606c), fusing a benzene ring to the selected bond (icon 606d), fusing a cyclopropyl ring to the selected bond (icon 606e), fusing a cyclooctane ring to the selected bond (icon 606f), fusing a cycloheptane ring to the selected bond (icon 606g), changing the selected bond to a triple bond (icon 606h), changing the selected bond to a double bond (icon 606i), fusing a 4-carbon ring to the selected bond (icon 606j), fusing a cyclopentane ring to the selected bond (icon 606k), fusing a cyclohexane ring to the selected bond (icon 606l), changing the selected bond to a bold bond (icon 606m), changing the selected bond to a wavy bond (e.g., with an unknown bond type) (icon 606n), changing the selected bond to a dashed bond (e.g., a partial bond) (icon 606o), changing the selected bond to a hashed wedged bond (e.g., a bond below the plane of the molecule) (icon 606p), and changing the selected bond to a wedged bond (e.g., a bond above the plane of the molecule) (icon 606q).

Figure 6B:
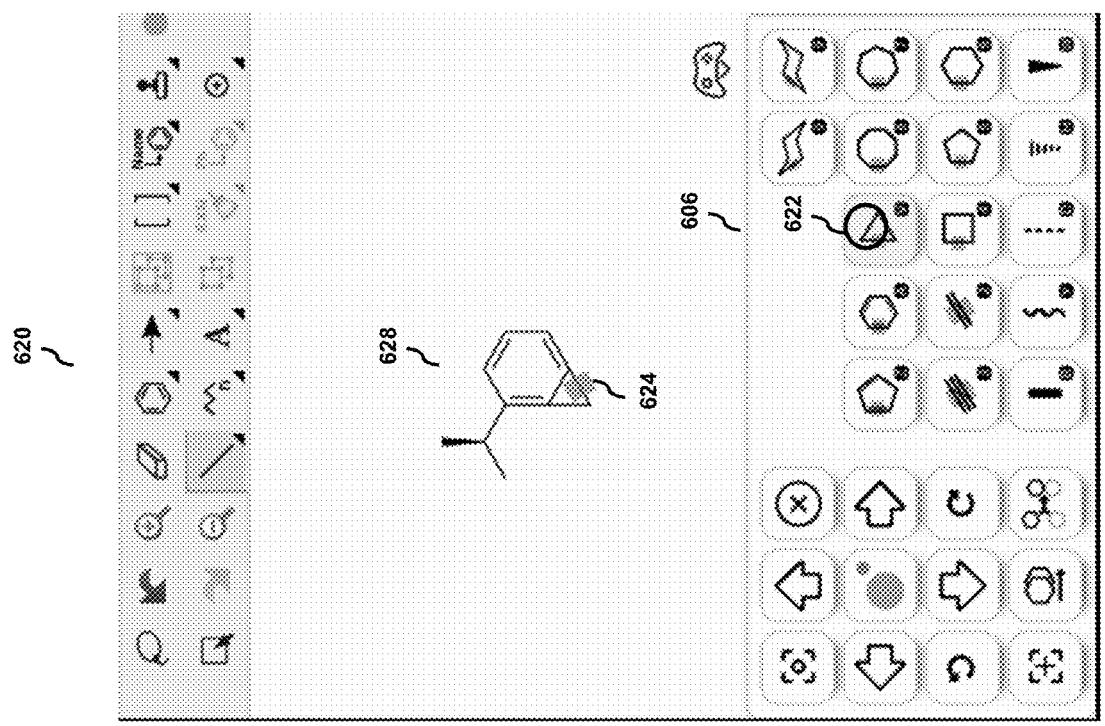
Figure 6C:
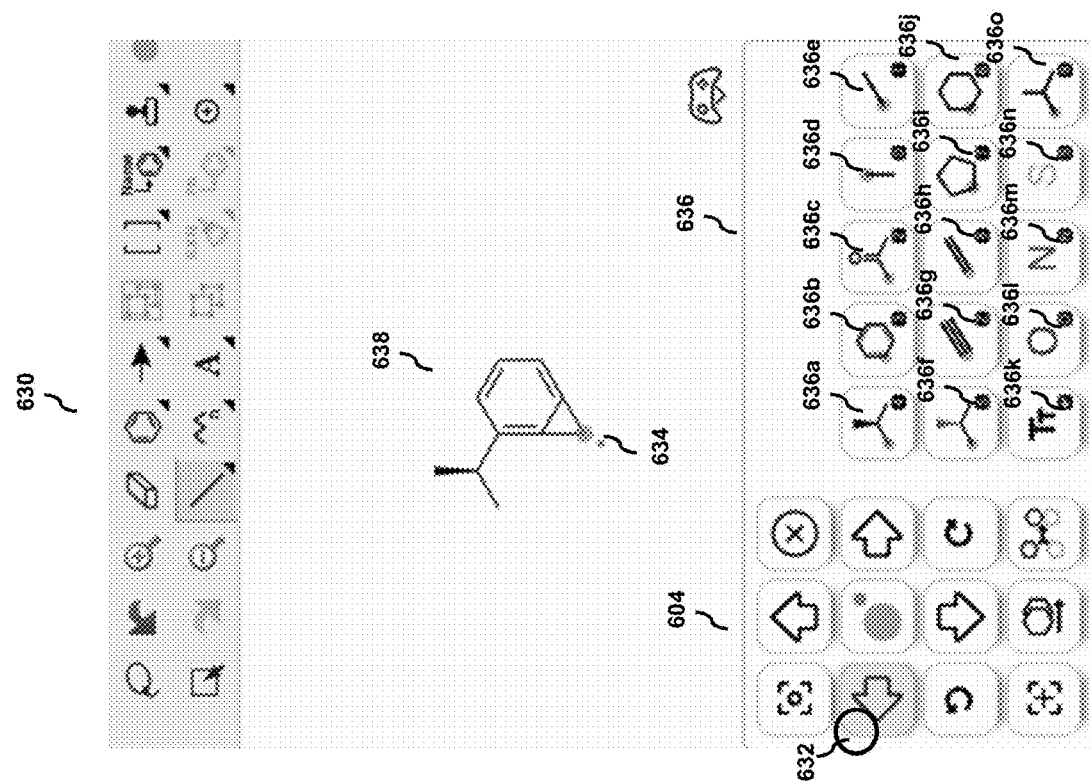
Figure 6D:
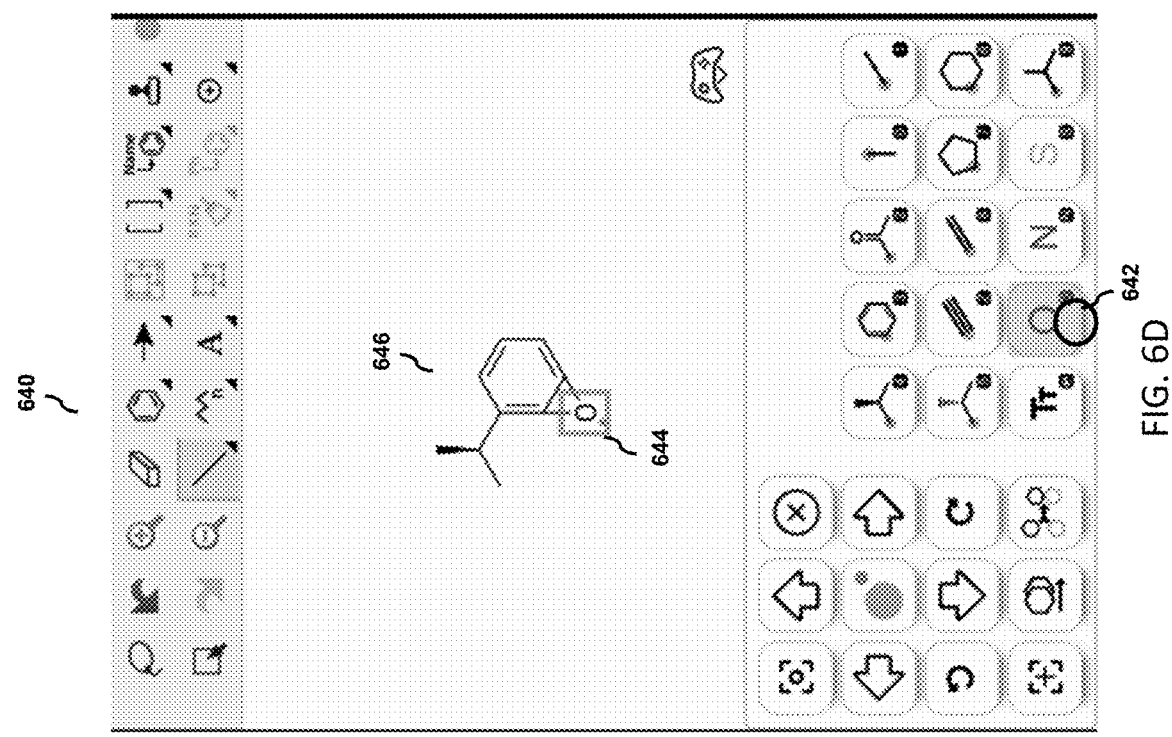

FIG. 6B through 6D show a progression of screenshots acquired while a user edited chemical structure 608 (from FIG. 6A) using the context-aware virtual keyboard. FIG. 6B shows a screenshot 620 just after the user pressed the selection control panel 606 at position 622, corresponding to fusing a cyclopropyl ring to the selected bond (icon 606e) from FIG. 6A. Responsive to this touch-based input by the user, a cyclopropyl ring was fused to the bond at navigation position 610 of FIG. 6A. The navigation position then shifted to location 624 on chemical structure representation 628 of FIG. 6B.

Referring now to screenshot 630 shown in FIG. 6C, the user pressed the navigation control panel 604 near location 632, moving the navigation position to the left on the chemical structure to location 634. Position 634 corresponds to a carbon atom in the recently added cyclopropyl ring. Upon moving the navigation position to location 634 on chemical structure 638, the selection control panel 636 was automatically updated to include a different set of action buttons relevant to the selected atom. The updated selection control panel 636 included action buttons for sprouting an isopropyl group with an out of the plane carbon (icon 636a), sprouting a benzene ring (icon 636b), sprouting a carbonyl group (icon 636c), sprouting a single bond (icons 636d and 636e), sprouting an isopropyl group with an into the plane carbon (icon 636f), sprouting a triple bond (icon 636g), sprouting a double bond (icon 636h), sprouting a 5-carbon ring (icon 636i), sprouting a 6-carbon ring (icon 636j), sprouting a text entry (icon 636k), sprouting an oxygen atom ("O") (icon 636l), sprouting a nitrogen atom ("N") (icon 636m), sprouting a sulfur atom ("S") (icon 636n), and sprouting an isopropyl group (icon 636o).

FIG. 6D shows a screenshot 640 just after the user pressed the display at position 642, corresponding to the selection of action button 636l (from FIG. 6C) for sprouting an oxygen atom. Upon selection of this action button, an oxygen atom 644 was added to chemical structure 646.

Example 2: Creating a Graphical Representation of a Reaction

The following example demonstrates how a user can rapidly and intuitively create a graphical representation of a chemical reaction using an embodiment of the context-aware virtual keyboard described herein.

Figure 7A:
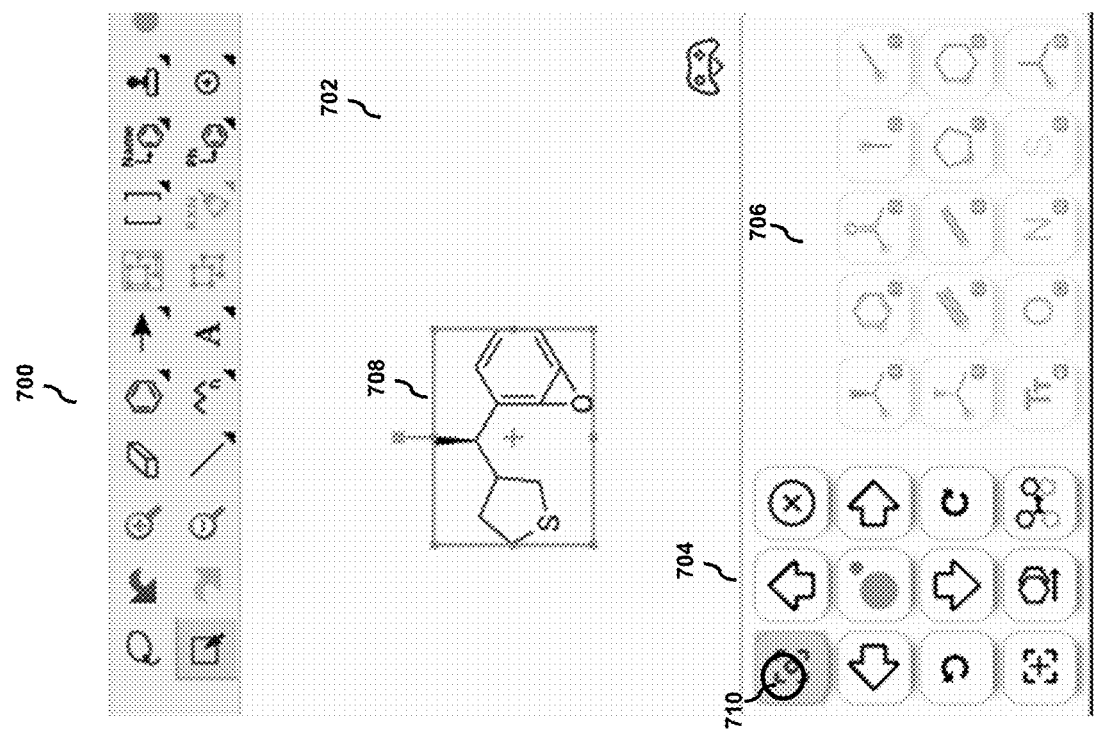
FIG. 7A, FIG. 7B, and FIG. 7C show screenshots of a context-aware virtual keyboard acquired while a user created a representation of a chemical reaction, according to an illustrative embodiment.
Figure 7B:
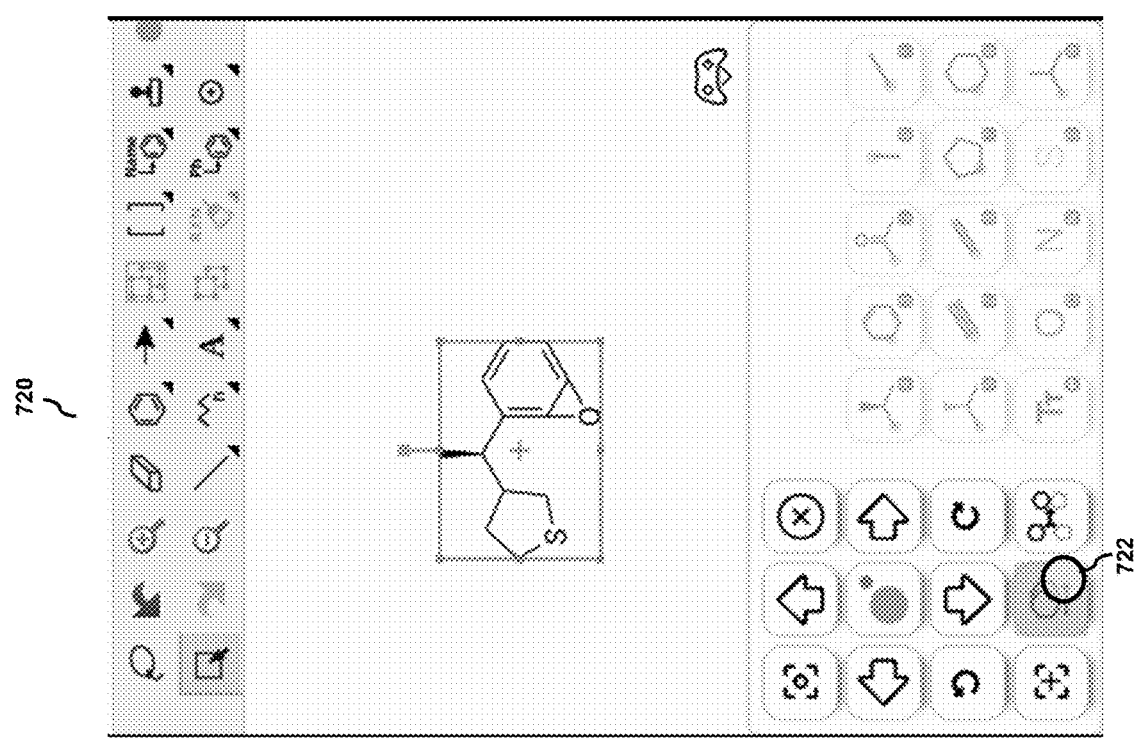
Figure 7C:
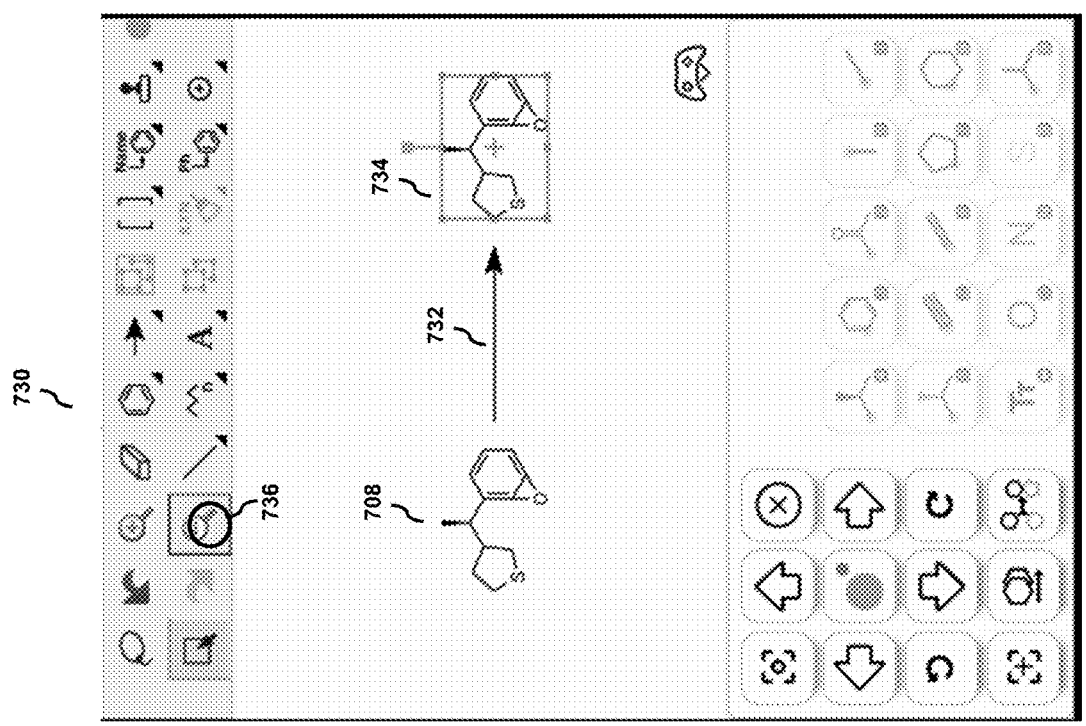

FIG. 7A through 7C show screenshots of the context-aware virtual keyboard which were acquired while a user created a graphical representation of a chemical reaction. FIG. 7A shows a screenshot 700 of the context-aware virtual keyboard. A user of the context-aware virtual keyboard pressed the navigation control panel 704 near position 710 to choose object selection icon 604a from FIG. 6A. Upon the selection of this icon, all of chemical structure 708 was selected in canvas panel 702. After chemical structure 708 was selected, the action buttons in selection control panel 706 became inactive (e.g., "grayed out") because the actions were no longer relevant to the selection.

Screenshot 720 shown in FIG. 7B shows the context-aware virtual keyboard after the user pressed the navigation control panel near position 722 (corresponding to the selection of reaction creation icon 604k from FIG. 6A) to quickly create a reaction drawing. Screenshot 730 shown in FIG. 7C was acquired soon after the user pressed the reaction creation icon (604k from FIG. 6A). A reaction arrow 732 was appended to the right of the original chemical structure 708, and a copy 734 of molecular structure 708 was appended to the right of reaction arrow 732. This approach allows a user to quickly and intuitively create a graphical representation of a chemical reaction. To obtain the view shown in screenshot 730, the user also pressed the screen near position 736 (corresponding to zoom-out icon 612m from FIG. 6A) to provide a wider field of view for the drawing.

Example 3: Repositioning a Graphical Representation of a Chemical Structure

The following example demonstrates how a user can reposition a graphical representation of a chemical reaction using an embodiment of the context-aware virtual keyboard described herein.

Figure 8:
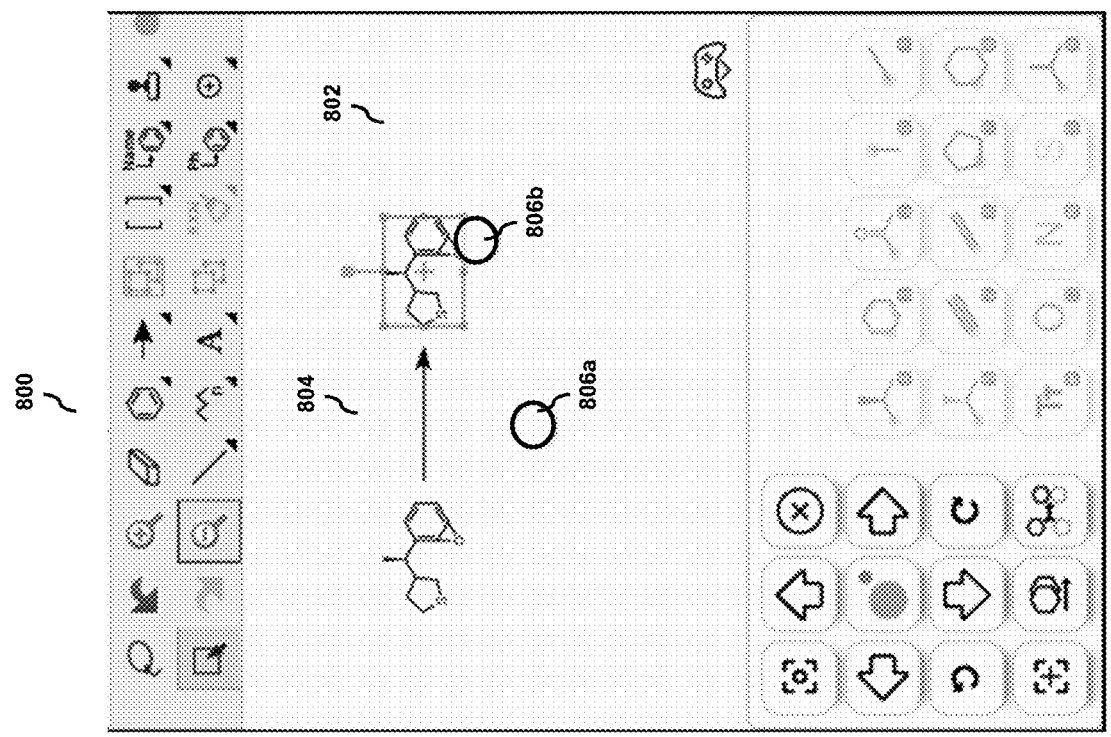

FIG. 8 shows an example screenshot 800 acquired while a user repositioned a graphical representation of a chemical reaction 804 using the context-aware virtual keyboard. In this illustrative example, the user placed two fingers on the touchscreen display, contacting the canvas panel 802 near positions 806a and 806b. The user then slid his/her fingers along the surface of the screen to reposition the graphical representation of the chemical reaction.

Example 4: Selecting Multiple Portions of a Graphical Representation of Chemical Structure The following example demonstrates how a user can intuitively select multiple portions of a graphical representation of a chemical structure using an embodiment of the context-aware virtual keyboard described herein.

FIGS. 9A and 9B show screenshots acquired while a user manually selected portions (e.g., all in this example) of a graphical representation of a chemical reaction. As shown in screenshot 900 (FIG. 9A), the user had previously selected the selection icon 910 (e.g., marquee icon 612k from FIG. 6A). The user then used his/her finger to select a rectangular portion 904 of canvas panel 902. In this example, the user had pressed the screen near location 906 and dragged her/his finger diagonally across the screen to position 908. The finger of the user was in contact with the touchscreen near position 908 when this screenshot was acquired. FIG. 9B shows screenshot 920, which was acquired after the reaction creation icon (604k from FIG. 6A) was selected. To select this reaction, the user expanded the selection box 904 of FIG. 9A to select chemical structures 922 and 926 and reaction arrow 924 of FIG. 9B.

Example 5: Navigating to a Bond and Deleting the Bond

The following example demonstrates how a user can choose a navigation position by manually selecting a region of the graphical representation before "fine-tuning" the navigation position using the navigation control panel of an illustrative embodiment of the context-aware virtual keyboard. The chemical bond associated with the selected navigation position was then deleted. FIG. 10A through 10C show screenshots acquired while a user performed these actions using an embodiment of the context-aware virtual keyboard.

FIG. 10A shows a screenshot 1000 of a graphical representation of a chemical reaction 1006 in canvas panel 1002. In this example, the user contacted his/her finger to the screen near position 1008 of the touchscreen device displaying the context-aware virtual keyboard. Since the area that the finger contacts near position 1008 is larger than a single navigation position (e.g., larger than a single atom or chemical bond in the representation), it was difficult for the user to select a particular bond or atom in the chemical structure 1004.

In this example, the user manually selected the oxygen atom surrounded by a box by tapping his/her finger near position 1008. However, the user desired to select one of the bonds connecting the oxygen to the adjacent benzene ring. As shown in screenshot 1020 of FIG. 10B, the user then utilized navigation control panel 1024 to fine-tune his/her selection and select the desired bond at navigation position 1028. To do this, the user contacted a finger to the touchscreen in the navigation control panel 1024 region of the screen near position 1022 to select the right navigational arrow icon (604f of FIG. 6A). Upon selecting this navigation button, the navigation position moved to the right to location 1028, corresponding to the bond that the user wanted to delete.

FIG. 10C shows screenshot 1030 which was acquired just after the user deleted the selected bond. To delete this bond, the user contacted his/her finger to the navigation panel 1034 near position 1036 (corresponding to the selection of the delete icon 604c from FIG. 6A). Upon selecting the delete icon, the bond was removed from the representation, and the oxygen atom (O) became a hydroxy (—OH) group 1038. The navigation position was then automatically moved to this newly added hydroxy group 1038, and the selection control panel 1042 was updated to include a set of updated action buttons that could be used to modify hydroxy group 1038.

System and Networking

As shown in FIG. 12, an implementation of a network environment 1200 for use in providing systems, methods, and apparatus for creating and/or editing a graphical representation of a chemical structure using a context-aware virtual keyboard as described herein is shown and described. In brief overview, referring now to FIG. 12, a block diagram of an exemplary cloud computing environment 1200 is shown and described. The cloud computing environment 1200 may include one or more resource providers 1202a, 1202b, 1202c (collectively, 1202). Each resource provider 1202 may include computing resources. In some implementations, computing resources may include any hardware and/or software used to process data. For example, computing resources may include hardware and/or software capable of executing algorithms, computer programs, and/or computer applications. In some implementations, exemplary computing resources may include application servers and/or databases with storage and retrieval capabilities. Each resource provider 1202 may be connected to any other resource provider 1202 in the cloud computing environment 1200. In some implementations, the resource providers 1202 may be connected over a computer network 1208. Each resource provider 1202 may be connected to one or more computing device 1204a, 1204b, 1204c (collectively, 1204), over the computer network 1208.

The cloud computing environment 1200 may include a resource manager 1206. The resource manager 1206 may be connected to the resource providers 1202 and the computing devices 1204 over the computer network 1208. In some implementations, the resource manager 1206 may facilitate the provision of computing resources by one or more resource providers 1202 to one or more computing devices 1204. The resource manager 1206 may receive a request for a computing resource from a particular computing device 1204. The resource manager 1206 may identify one or more resource providers 1202 capable of providing the computing resource requested by the computing device 1204. The resource manager 1206 may select a resource provider 1202 to provide the computing resource. The resource manager 1206 may facilitate a connection between the resource provider 1202 and a particular computing device 1204. In some implementations, the resource manager 1206 may establish a connection between a particular resource provider 1202 and a particular computing device 1204. In some implementations, the resource manager 1206 may redirect a particular computing device 1204 to a particular resource provider 1202 with the requested computing resource.

FIG. 13 shows an example of a computing device 1300 and a mobile computing device 1350 that can be used to implement the techniques described in this disclosure. The computing device 1300 is intended to represent various forms of digital computers, such as laptops, desktops, workstations, personal digital assistants, servers, blade servers, mainframes, and other appropriate computers. The mobile computing device 1350 is intended to represent various forms of mobile devices, such as personal digital assistants, cellular telephones, smartphones, and other similar computing devices. The components shown here, their connections and relationships, and their functions, are meant to be examples only, and are not meant to be limiting.

The computing device 1300 includes a processor 1302, a memory 1304, a storage device 1306, a high-speed interface 1308 connecting to the memory 1304 and multiple high-speed expansion ports 1310, and a low-speed interface 1312 connecting to a low-speed expansion port 1314 and the storage device 1306. Each of the processor 1302, the memory 1304, the storage device 1306, the high-speed interface 1308, the high-speed expansion ports 1310, and the low-speed interface 1312, are interconnected using various busses, and may be mounted on a common motherboard or in other manners as appropriate. The processor 1302 can process instructions for execution within the computing device 1300, including instructions stored in the memory 1304 or on the storage device 1306 to display graphical information for a GUI on an external input/output device, such as a display 1316 coupled to the high-speed interface 1308. In other implementations, multiple processors and/or multiple buses may be used, as appropriate, along with multiple memories and types of memory. Also, multiple computing devices may be connected, with each device providing portions of the necessary operations (e.g., as a server bank, a group of blade servers, or a multi-processor system). Thus, as the term is used herein, where a plurality of functions are described as being performed by "a processor", this encompasses embodiments wherein the plurality of functions are performed by any number of processors (one or more) of any number of computing devices (one or more). Furthermore, where a function is described as being performed by "a processor", this encompasses embodiments wherein the function is performed by any number of processors (one or more) of any number of computing devices (one or more) (e.g., in a distributed computing system).

The memory 1304 stores information within the computing device 1300. In some implementations, the memory 1304 is a volatile memory unit or units. In some implementations, the memory 1304 is a non-volatile memory unit or units. The memory 1304 may also be another form of computer-readable medium, such as a magnetic or optical disk.

The storage device 1306 is capable of providing mass storage for the computing device 1300. In some implementations, the storage device 1306 may be or contain a computer-readable medium, such as a floppy disk device, a hard disk device, an optical disk device, or a tape device, a flash memory or other similar solid state memory device, or an array of devices, including devices in a storage area network or other configurations. Instructions can be stored in an information carrier. The instructions, when executed by one or more processing devices (for example, processor 1302), perform one or more methods, such as those described above. The instructions can also be stored by one or more storage devices such as computer- or machine-readable mediums (for example, the memory 1304, the storage device 1306, or memory on the processor 1302).

The high-speed interface 1308 manages bandwidth-intensive operations for the computing device 1300, while the low-speed interface 1312 manages lower bandwidth-intensive operations. Such allocation of functions is an example only. In some implementations, the high-speed interface 1308 is coupled to the memory 1304, the display 1316 (e.g., through a graphics processor or accelerator), and to the high-speed expansion ports 1310, which may accept various expansion cards (not shown). In the implementation, the low-speed interface 1312 is coupled to the storage device 1306 and the low-speed expansion port 1314. The low-speed expansion port 1314, which may include various communication ports (e.g., USB, Bluetooth®, Ethernet, wireless Ethernet) may be coupled to one or more input/output devices, such as a keyboard, a pointing device, a scanner, or a networking device such as a switch or router, e.g., through a network adapter.

The computing device 1300 may be implemented in a number of different forms, as shown in the figure. For example, it may be implemented as a standard server 1320, or multiple times in a group of such servers. In addition, it may be implemented in a personal computer such as a laptop computer 1322. It may also be implemented as part of a rack server system 1324. Alternatively, components from the computing device 1300 may be combined with other components in a mobile device (not shown), such as a mobile computing device 1350. Each of such devices may contain one or more of the computing device 1300 and the mobile computing device 1350, and an entire system may be made up of multiple computing devices communicating with each other.

The mobile computing device 1350 includes a processor 1352, a memory 1364, an input/output device such as a display 1354, a communication interface 1366, and a transceiver 1368, among other components. The mobile computing device 1350 may also be provided with a storage device, such as a micro-drive or other device, to provide additional storage. Each of the processor 1352, the memory 1364, the display 1354, the communication interface 1366, and the transceiver 1368, are interconnected using various buses, and several of the components may be mounted on a common motherboard or in other manners as appropriate.

The processor 1352 can execute instructions within the mobile computing device 1350, including instructions stored in the memory 1364. The processor 1352 may be implemented as a chipset of chips that include separate and multiple analog and digital processors. The processor 1352 may provide, for example, for coordination of the other components of the mobile computing device 1350, such as control of user interfaces, applications run by the mobile computing device 1350, and wireless communication by the mobile computing device 1350.

The processor 1352 may communicate with a user through a control interface 1358 and a display interface 1356 coupled to the display 1354. The display 1354 may be, for example, a TFT (Thin-Film-Transistor Liquid Crystal Display) display or an OLED (Organic Light Emitting Diode) display, or other appropriate display technology. The display interface 1356 may comprise appropriate circuitry for driving the display 1354 to present graphical and other information to a user. The control interface 1358 may receive commands from a user and convert them for submission to the processor 1352. In addition, an external interface 1362 may provide communication with the processor 1352, so as to enable near area communication of the mobile computing device 1350 with other devices. The external interface 1362 may provide, for example, for wired communication in some implementations, or for wireless communication in other implementations, and multiple interfaces may also be used.

The memory 1364 stores information within the mobile computing device 1350. The memory 1364 can be implemented as one or more of a computer-readable medium or media, a volatile memory unit or units, or a non-volatile memory unit or units. An expansion memory 1374 may also be provided and connected to the mobile computing device 1350 through an expansion interface 1372, which may include, for example, a SIMM (Single In Line Memory Module) card interface. The expansion memory 1374 may provide extra storage space for the mobile computing device 1350, or may also store applications or other information for the mobile computing device 1350. Specifically, the expansion memory 1374 may include instructions to carry out or supplement the processes described above, and may include secure information also. Thus, for example, the expansion memory 1374 may be provide as a security module for the mobile computing device 1350, and may be programmed with instructions that permit secure use of the mobile computing device 1350. In addition, secure applications may be provided via the SIMM cards, along with additional information, such as placing identifying information on the SIMM card in a non-hackable manner.

The memory may include, for example, flash memory and/or NVRAM memory (non-volatile random access memory), as discussed below. In some implementations, instructions are stored in an information carrier. that the instructions, when executed by one or more processing devices (for example, processor 1352), perform one or more methods, such as those described above. The instructions can also be stored by one or more storage devices, such as one or more computer- or machine-readable mediums (for example, the memory 1364, the expansion memory 1374, or memory on the processor 1352). In some implementations, the instructions can be received in a propagated signal, for example, over the transceiver 1368 or the external interface 1362.

The mobile computing device 1350 may communicate wirelessly through the communication interface 1366, which may include digital signal processing circuitry where necessary. The communication interface 1366 may provide for communications under various modes or protocols, such as GSM voice calls (Global System for Mobile communications), SMS (Short Message Service), EMS (Enhanced Messaging Service), or MMS messaging (Multimedia Messaging Service), CDMA (code division multiple access), TDMA (time division multiple access), PDC (Personal Digital Cellular), WCDMA (Wideband Code Division Multiple Access), CDMA2000, or GPRS (General Packet Radio Service), among others. Such communication may occur, for example, through the transceiver 1368 using a radio-frequency. In addition, short-range communication may occur, such as using a Bluetooth®, Wi-Fi™, or other such transceiver (not shown). In addition, a GPS (Global Positioning System) receiver module 1370 may provide additional navigation- and location-related wireless data to the mobile computing device 1350, which may be used as appropriate by applications running on the mobile computing device 1350.

The mobile computing device 1350 may also communicate audibly using an audio codec 1360, which may receive spoken information from a user and convert it to usable digital information. The audio codec 1360 may likewise generate audible sound for a user, such as through a speaker, e.g., in a handset of the mobile computing device 1350. Such sound may include sound from voice telephone calls, may include recorded sound (e.g., voice messages, music files, etc.) and may also include sound generated by applications operating on the mobile computing device 1350.

The mobile computing device 1350 may be implemented in a number of different forms, as shown in the figure. For example, it may be implemented as a cellular telephone 1380. It may also be implemented as part of a smart-phone 1382, personal digital assistant, or other similar mobile device.

Various implementations of the systems and techniques described here can be realized in digital electronic circuitry, integrated circuitry, specially designed ASICs (application specific integrated circuits), computer hardware, firmware, software, and/or combinations thereof. These various implementations can include implementation in one or more computer programs that are executable and/or interpretable on a programmable system including at least one programmable processor, which may be special or general purpose, coupled to receive data and instructions from, and to transmit data and instructions to, a storage system, at least one input device, and at least one output device.

These computer programs (also known as programs, software, software applications or code) include machine instructions for a programmable processor, and can be implemented in a high-level procedural and/or object-oriented programming language, and/or in assembly/machine language. As used herein, the terms machine-readable medium and computer-readable medium refer to any computer program product, apparatus and/or device (e.g., magnetic discs, optical disks, memory, Programmable Logic Devices (PLDs)) used to provide machine instructions and/or data to a programmable processor, including a machine-readable medium that receives machine instructions as a machine-readable signal. The term machine-readable signal refers to any signal used to provide machine instructions and/or data to a programmable processor.

To provide for interaction with a user, the systems and techniques described here can be implemented on a computer having a display device (e.g., a CRT (cathode ray tube) or LCD (liquid crystal display) monitor) for displaying information to the user and a keyboard and a pointing device (e.g., a mouse or a trackball) by which the user can provide input to the computer. Other kinds of devices can be used to provide for interaction with a user as well; for example, feedback provided to the user can be any form of sensory feedback (e.g., visual feedback, auditory feedback, or tactile feedback); and input from the user can be received in any form, including acoustic, speech, or tactile input.

The systems and techniques described here can be implemented in a computing system that includes a back end component (e.g., as a data server), or that includes a middleware component (e.g., an application server), or that includes a front end component (e.g., a client computer having a graphical user interface or a Web browser through which a user can interact with an implementation of the systems and techniques described here), or any combination of such back end, middleware, or front end components. The components of the system can be interconnected by any form or medium of digital data communication (e.g., a communication network). Examples of communication networks include a local area network (LAN), a wide area network (WAN), and the Internet.

The computing system can include clients and servers. A client and server are generally remote from each other and typically interact through a communication network. The relationship of client and server arises by virtue of computer programs running on the respective computers and having a client-server relationship to each other.

FIG. 14 depicts an example system 1400 for drawing and/or editing graphical representations of chemical structures. The system 1400 includes client nodes 1402a and 1402b, a server node 1404, a database 1406, and, for enabling communications therebetween, a network 1408. As illustrated, the server node 1404 may include a drawing module 1410.

The network 1408 may be, for example, a local-area network (LAN), such as a company or laboratory Intranet, a metropolitan area network (MAN), or a wide area network (WAN), such as the Internet. Each of the client nodes 1402, server node 1404, and the database 1406 may be connected to the network 1408 through a variety of connections including, but not limited to, standard telephone lines, LAN or WAN links (e.g., T1, T3, 56 kb, X.25), broadband connections (e.g., ISDN, Frame Relay, ATM), or wireless connections. The connections, moreover, may be established using a variety of communication protocols (e.g., HTTP, TCP/IP, IPX, SPX, NetBIOS, NetBEUI, SMB, Ethernet, ARCNET, Fiber Distributed Data Interface (FDDI), RS232, IEEE 802.11, IEEE 802.11a, IEEE 802.11b, IEEE 802.11g, and direct asynchronous connections).

The client node 1402a may be any type of wireless device, information appliance, tablet computer, personal digital assistant, cellular phone, handheld device, or other portable computing device that is capable of both presenting information/data to, and receiving commands from, a user of the client node 1402a (e.g., an analytical chemist). Similarly, the client node 1402b may be any type of personal computer, Windows-based terminal, network computer, wireless device, information appliance, RISC Power PC, X-device, workstation, mini computer, main frame computer, set top box, or other computing device that is capable of both presenting information/data to, and receiving commands from, a user of the client node 1402b. The client nodes 1402 may include, for example, a graphical display device (e.g., a touchscreen or a computer monitor), a data entry device (e.g., a keyboard, a touchscreen, or a mouse pad), persistent and/or volatile storage (e.g., computer memory), and a processor. In one embodiment, the client node 1402 includes a web browser, such as, for example, Internet Explorer® developed by Microsoft Corporation of Redmond, Wash., to connect to the World Wide Web.

For its part, the server node 1404 may be any computing device that is capable of receiving information/data from and delivering information/data to the client nodes 1402, for example over the network 1408, and that is capable of querying, receiving information/data from, and delivering information/data to the server node 1404. For example, as further explained below, the server node 1404 may receive input (e.g., a multi-touch gesture) from a user of the client node 1402, create or edit a chemical structure representation according to the input, and present or display the chemical structure representation to the user at the client node 1402. The server node 1404 may include a processor and persistent and/or volatile storage, such as computer memory.

The server node 1404 may be any computing device that is capable of storing and managing collections of data, such as data relating to chemical structure representations. The chemical structure representations may be, for example, of the type described in related U.S. Pat. No. 8,433,723, filed May 3, 2011, titled "Systems, Methods, and Apparatus for Processing Documents to Identify Structures," related U.S. Pat. No. 8,538,983, filed, Sep. 21, 2011, titled "Systems, Methods, and Apparatus for Facilitating Chemical Analyses," related International Patent Application No. PCT/US12/26574, filed Feb. 24, 2012, titled "Systems, Methods, and Apparatus for Drawing Chemical Structures Using Touch and Gestures," and related U.S. Pat. No. 9,535,583, filed Dec. 13, 2012, titled "Draw-ahead Feature for Chemical Structure Drawing Applications," the disclosures of each of which are hereby incorporated by reference herein in their entireties.

As used herein, the term "server node" is broadly used to refer to any repository of information. The data stored within the server node 1404 may be harvested from the server node 1404 in any manner. In one embodiment, the harvesting is performed utilizing indexing and structure recognition algorithms, and the harvested data is connected together by examining and correlating the disjointed information that is found.

The drawing module 1410 of the server node 1404 may be implemented as any software program and/or hardware device, for example an application specific integrated circuit (ASIC) or a field programmable gate array (FPGA), that is capable of providing the functionality described herein. It will be understood by one having ordinary skill in the art, however, that the illustrated module 1410, and the organization of the server node 1404, are conceptual, rather than explicit, requirements. For example, it should be understood that the drawing module 1410 may in fact be implemented as multiple modules, such that the functions performed by the single module, as described herein, are in fact performed by the multiple modules.

Although not shown in FIG. 14, any or all of the client nodes 1402, the server node 1404, and the database 1406 may also include its own transceiver (or separate receiver and transmitter) that is capable of receiving and transmitting communications, including requests, responses, and commands, such as, for example, inter-processor communications and networked communications. The transceivers (or separate receivers and transmitters) may each be implemented as a hardware device, or as a software module with a hardware interface.

It will also be understood by those skilled in the art that FIG. 14 is a simplified illustration of the system 1400 and that it is depicted as such to facilitate the explanation of various embodiments of the present disclosure. Moreover, the system 1400 may be modified in a variety of manners without departing from the spirit and scope of the present disclosure. For example, rather than being implemented on a single server node 1404, the drawing module 1410 may instead be implemented on a different computing device (not shown) and such computing devices may communicate with one another directly, over the network 1408, or over another additional network (not shown). In yet another example, the functionality of the server node 1404 may in fact be resident on the server node 1404 (e.g., be implemented in the computer memory thereof). Additional options are for the server node 1404 and/or the database 1406 to be local to the client node 1402 (such that they may all communicate directly without using the network 1408), or for the functionality of the server node 1404 and/or the database 1406 to be implemented on the client node 1402 (e.g., for the drawing module 1410 and/or the server node 1404 to reside on the client node 1402). As such, the depiction of the system 1400 in FIG. 14 is non-limiting.

In certain embodiments, the system 1400 allows a user to draw and edit a chemical structure representation using one or more fingers on an input interface, such as a touchpad or touchscreen, at the client tablet node 1402a. The system 1400, in some embodiments, allows a user to draw and edit a graphical representation of a chemical structure using a mouse, stylus, keypad, trackball, or other input interface, such as an input interface at a client personal computer 1402b. The input interface, in some implementations, may include a natural language processing module capable of converting utterances to a series of commands for activating controls of the user interface.

In general, the drawing module 1410 in the server node 1404 is configured to draw or revise the chemical structure representation according to the input from the user, as explained above with respect to the prior figures. The drawing module 1410 may then provide an image (e.g., a collection of pixels) of the graphical representation of the chemical structure for presentation to the user on the graphical display of the particular client node 1402. In general, the system 1400 may be used to perform any of the methods described herein.

Elements of different implementations described herein may be combined to form other implementations not specifically set forth above. Elements may be left out of the processes, computer programs, databases, etc. described herein without adversely affecting their operation. In addition, the logic flows depicted in the figures do not require the particular order shown, or sequential order, to achieve desirable results. Various separate elements may be combined into one or more individual elements to perform the functions described herein.

Throughout the description, where apparatus and systems are described as having, including, or comprising specific components, or where processes and methods are described as having, including, or comprising specific steps, it is contemplated that, additionally, there are apparatus, and systems of the present invention that consist essentially of, or consist of, the recited components, and that there are processes and methods according to the present invention that consist essentially of, or consist of, the recited processing steps.

It should be understood that the order of steps or order for performing certain action is immaterial so long as the invention remains operable. Moreover, two or more steps or actions may be conducted simultaneously.

While the invention has been particularly shown and described with reference to specific preferred embodiments, it should be understood by those skilled in the art that various changes in form and detail may be made therein without departing from the spirit and scope of the invention as defined by the appended claims.

What is claimed:

1. An apparatus for creating and/or editing a graphical representation of a chemical structure using a context-aware virtual keyboard, the apparatus comprising: a memory for storing a set of instructions; and a processor for executing the set of instructions, wherein the instructions, when executed, cause the processor to: provide a graphical representation of at least a portion of an in-progress chemical structure for presentation on a graphical display in a canvas panel of the context-aware virtual keyboard; receive an input, from a navigation control panel of the context-aware virtual keyboard, corresponding to a selection of a navigation position, wherein the navigation position corresponds to the location of an atom, a chemical bond, a chemical structure portion, or a reaction arrow in the graphical representation; identify, based at least in part on the selected navigation position, a set of candidate actions and display the set of candidate actions on the graphical display in a selection control panel of the context-aware virtual keyboard; receive an input from the selection control panel of the context-aware virtual keyboard corresponding to a selection of an action from the set of candidate actions; and update the graphical representation based on the selected action by at least one or more of: (i) appending a chemical structure associated with the selected action to the in-progress chemical structure at an atom, chemical bond, or chemical structure portion corresponding to the navigation position, (ii) replacing or partially replacing the atom, chemical bond, or chemical structure portion corresponding to the navigation position in the in-progress chemical structure with the chemical structure associated with the selected action, and (iii) modifying the atom, chemical bond, chemical structure portion, or a reaction arrow corresponding to the navigation position in the in-progress chemical structure according to the selected action.

2. The apparatus of claim 1, wherein each action of the set of candidate actions corresponds to a modification to the location of the atom, chemical bond, chemical structure portion, or reaction arrow corresponding to the selected navigation position.

3. The apparatus of claim 1, wherein the set of candidate actions comprise one or more members selected from the group consisting of (i) adding a carbon ring, (ii) adding a chemical bond, (iii) adding an atom, (iv) adding a text entry, (v) changing a bond angle, (vi) changing a chemical bond type, (vii) rotating a chemical bond by an angle, and (viii) flipping a chemical bond around an axis.

4. The apparatus of claim 1, wherein the instructions, when executed, cause the processor to update the set of candidate actions in real-time based on the selected navigation position.

5. The apparatus of claim 1, wherein, when the navigation position corresponds to the location of an atom, the set of candidate actions comprise one or more members selected from the group consisting of (i) adding a carbon ring, (ii) adding a chemical bond, (iii) adding an atom, and (iv) adding a text entry.

6. The apparatus of claim 1, wherein, when the navigation position corresponds to the location of a first chemical bond, the set of candidate actions comprise one or more members selected from the group consisting of (i) adding a carbon ring, (ii) adding a second chemical bond, (iii) adding an atom, (iv) adding a text entry, (v) changing an angle of the first chemical bond, (vi) changing a bond type of the first chemical bond, (vii) rotating the first chemical bond by an angle, and (viii) flipping the first chemical bond around an axis.

7. The apparatus of claim 1, wherein, when the navigation position corresponds to the location of a chemical structure portion, the set of candidate actions comprise one or more members selected from the group consisting of (i) selecting a different chemical structure portion, (ii) creating a reaction, (iii) duplicating the chemical structure portion, and (iv) joining the chemical structure portion to a different chemical structure portion at a bond or atom.

8. The apparatus of claim 1, wherein, when the navigation position corresponds to the location of a reaction arrow, the set of candidate actions comprise one or more members selected from the group consisting of (i) adding reaction conditions and (ii) adding associated reagents and/or reactants.

9. The apparatus of claim 1, wherein each action of the set of candidate actions is derived from an evaluation of whether it is chemically feasible to (i) append, to an atom, bond, or chemical structure portion associated with the selected navigation position, a chemical structure associated with the action or (ii) replace or partially replace the atom, bond, or chemical structure portion associated with the selected navigation position with the atom, bond, or chemical structure portion structure associated with the action.

10. The apparatus of claim 1, wherein the instructions, when executed, cause the processor to arrange the set of candidate actions in a ranked order for rendering on the graphical display.

11. The apparatus of claim 1, wherein the instructions, when executed, cause the processor to:
identify a plurality of predictive actions, wherein each predictive action of the plurality of predictive actions is derived from a database and/or based on a frequency of use by one or more users; and
display one or more predictive actions from the plurality in or above the selection control panel of the context-aware virtual keyboard on the graphical display.

12. The apparatus of claim 11, wherein three or fewer predictive actions are displayed in or above the selection control panel of the context-aware virtual keyboard on the graphical display.

13. The apparatus of claim 11, wherein the instructions, when executed, cause the processor to display a chemical structure associated with one of the plurality of predictive actions as being appended to the in-progress chemical structure.

14. The apparatus of claim 1, wherein the canvas panel, navigation control panel, and selection control panel are displayed in separate windows on the graphical display.

15. The apparatus of claim 14, wherein the canvas panel is larger than the navigation control panel and the selection control panel.

16. The apparatus of claim 1, wherein the navigation control panel and selection control panel are overlaid over the canvas panel.

17. The apparatus of claim 1, wherein the navigation control panel comprises a plurality of navigation icons.

18. The apparatus of claim 17, wherein each of the plurality of navigation icons has a display area in a range from about 30 to about 50 pixels.

19. The apparatus of claim 1, wherein the navigation control panel comprises ancillary action buttons for one or more the actions selected from the group consisting of (i) deleting an atom, bond, or portion of the chemical structure corresponding to the navigation position, (ii) adding a reaction, (iii) undoing a previous action, (iv) redoing a previous action, and (v) selecting an atom, bond, or portion of the chemical structure.

20. The apparatus of claim 1, wherein the navigation control panel comprises 12 icons or fewer.

21. The apparatus of claim 1, wherein the selection control panel comprises 20 action icons or fewer.

22. The apparatus of claim 1, wherein the graphical display has a display region of about 700 $cm^2$ or less in area.

23. The apparatus of claim 1, wherein the graphical display has a display region of about 150 $cm^2$ or less in area.

24. The apparatus of claim 1, wherein the graphical display is a touchscreen.

25. The apparatus of claim 1, wherein the instructions, when executed, cause the processor to receive the input over a network, from a computing device.

26. The apparatus of claim 25, wherein the computing device is a cell phone or a tablet computer.

27. The apparatus of claim 1, wherein the instructions, when executed, cause the processor to:
receive an input from the selection control panel of the context-aware virtual keyboard corresponding to a selection of a portion of the in-progress chemical structure;
receive an input from the selection control panel of the context-aware virtual keyboard corresponding to a selection of a reaction icon; and
update the representation, based on the one or more selected portions and the selected reaction icon, by (i) appending an arrow to the right of the in-progress chemical structure and (ii) appending a copy of the selected portion to the right of the arrow.

28. The apparatus of claim 1, wherein the instructions, when executed, cause the processor to:
receive an input from the selection control panel of the context-aware virtual keyboard corresponding to a selection of two or more portions of the in-progress chemical structure;
receive an input from the selection control panel of the context-aware virtual keyboard corresponding to a selection of a reaction icon; and
update the representation, based on the one or more selected portions and the selected reaction icon, by (i) appending an arrow to the right of the in-progress chemical structure and (ii) appending a reaction product to the right of the arrow, wherein the reaction product corresponds to a chemical structure resulting from the reaction of the two or more selected portions and is derived from predefined chemical rules.

29. An apparatus for creating and/or editing a graphical representation of a chemical structure using a dual-display context-aware virtual keyboard, the apparatus comprising: a memory for storing a set of instructions; and a processor for executing the set of instructions, wherein the instructions, when executed, cause the processor to: provide a graphical representation of at least a portion of an in-progress chemical structure for presentation on a first graphical display; receive an input, from a computing device [e.g., a touchscreen device, e.g., a handheld touchscreen device displaying, on a second graphical display, a navigation control panel of the context-aware virtual keyboard, said input corresponding to a selection of a navigation position, wherein the navigation position corresponds to the location of an atom, bond, chemical structure portion, or reaction arrow in the graphical representation; identify, based on the selected navigation position, a set of candidate actions and display the set of candidate actions on the second graphical display in a selection control panel of the context-aware virtual keyboard; receive an input; via the selection control panel of the context-aware virtual keyboard displayed on the second graphical display, corresponding to a selection an action from the set of candidate actions; and update the graphical representation, displayed on the first graphical display; based on the selected action by at least one or more of: (i) appending a chemical structure associated with the selected action to the in-progress chemical structure at an atom, chemical bond, or chemical structure portion corresponding to the navigation position, (ii) replacing or partially replacing the atom, chemical bond, or chemical structure portion corresponding to the navigation position in the in-progress chemical structure with the chemical structure associated with the selected action, and (iii) modifying the atom, chemical bond, chemical structure portion, or a reaction arrow corresponding to the navigation position in the in-progress chemical structure according to the selected action.

30. The apparatus of claim 29, wherein the first graphical display has a display region of about 1400 $cm^2$ or greater in area.

31. The apparatus of claim 29, wherein the second graphical display has a display region of about 150 $cm^2$ or less in area.

32. The apparatus of claim 29, wherein the first graphical display is a computer monitor, a television, or a projected image.

33. The apparatus of claim 29, wherein the second graphical display is a touchscreen display of a mobile phone or a tablet computer.

34. A method of creating a graphical representation of a chemical structure using a context-aware virtual keyboard, the method comprising: providing, by a processor of a computing device, a graphical representation of at least a portion of an in-progress chemical structure for presentation on a graphical display in a canvas panel of the context-aware virtual keyboard; receiving, by the processor, an input, from a navigation control panel of the context-aware virtual keyboard, corresponding to a selection of a navigation position, wherein the navigation position corresponds to the location of an atom, a bond, a chemical structure portion, or a reaction arrow in the graphical representation; identifying, by the processor, based at least in part on the selected navigation position, a set of candidate actions and display the set of candidate actions on the graphical display in a selection control panel of the context-aware virtual keyboard: receiving, by the processor, an input from the selection control panel of the context-aware virtual keyboard corresponding to a selection of an action from the set of candidate actions; and updating, by the processor, the graphical representation based on the selected action by at least one or more of: (i) appending a chemical structure associated with the selected action to the in-progress chemical structure at an atom, chemical bond, or chemical structure portion corresponding to the navigation position, (ii) replacing or partially replacing the atom, chemical bond, or chemical structure portion corresponding to the navigation position in the in-progress chemical structure with the chemical structure associated with the selected action, and (iii) modifying the atom, chemical bond, chemical structure portion, or a reaction arrow corresponding to the navigation position in the in-progress chemical structure according to the selected action.

35. A method of creating a graphical representation of a chemical structure using a dual-display context-aware virtual keyboard, the method comprising: providing, by a processor of a computing device, a graphical representation of at least a portion of an in-progress chemical structure for presentation on a first graphical display; receiving, by the processor, an input, from a computing device displaying, on a second graphical display, a navigation control panel of the context-aware virtual keyboard, said input corresponding to a selection of a navigation position, wherein the navigation position corresponds to the location of an atom, bond, chemical structure portion, or reaction arrow in the graphical representation: identifying, by the processor, based on the selected navigation position, a set of candidate actions and displaying the set of candidate actions on the second graphical display in a selection control panel of the context-aware virtual keyboard; receiving, by the processor, an input, via the selection control panel of the context-aware virtual keyboard displayed on the second graphical display, corresponding to a selection of an action from the set of candidate actions; and updating, by the processor, the representation, displayed on the first graphical display, based on the selected action by at least one or more of: (i) appending a chemical structure associated with the selected action to the in-progress chemical structure at an atom, chemical bond, or chemical structure portion corresponding to the navigation position, (ii) replacing or partially replacing the atom, chemical bond, or chemical structure portion corresponding to the navigation position in the in-progress chemical structure with the chemical structure associated with the selected action, and (iii) modifying the atom, chemical bond, chemical structure portion, or a reaction arrow corresponding to the navigation position in the in-progress chemical structure according to the selected action.

* * * * *